(12) United States Patent
Hara et al.

(10) Patent No.: US 7,239,684 B2
(45) Date of Patent: Jul. 3, 2007

(54) RADIOTHERAPY APPARATUS MONITORING THERAPEUTIC FIELD IN REAL-TIME DURING TREATMENT

(75) Inventors: Kenji Hara, Hiroshima (JP); Makoto Akatsu, Hiroshima (JP); Noriyuki Kawata, Hiroshima (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 11/067,013

(22) Filed: Feb. 28, 2005

(65) Prior Publication Data

US 2006/0193435 A1 Aug. 31, 2006

(51) Int. Cl.
*A61N 5/10* (2006.01)
*A61B 5/05* (2006.01)
*A61B 6/00* (2006.01)

(52) U.S. Cl. .............................. 378/65; 600/427; 606/1

(58) Field of Classification Search ................ 378/4, 378/9, 11, 15, 19, 65, 92, 197, 198; 600/427; 606/33, 1; 315/500, 505; 607/101
See application file for complete search history.

(56) References Cited

U.S. PATENT DOCUMENTS

| | | | | |
|---|---|---|---|---|
| 3,082,322 A | * | 3/1963 | Koerner et al. | 378/65 |
| 3,398,375 A | * | 8/1968 | Haimson | 315/505 |
| 5,207,223 A | * | 5/1993 | Adler | 600/427 |
| 6,307,914 B1 | * | 10/2001 | Kunieda et al. | 378/65 |
| 6,590,958 B2 | * | 7/2003 | Barber et al. | 378/98.8 |

| | | | | |
|---|---|---|---|---|
| 2003/0048868 A1 | * | 3/2003 | Bailey et al. | 378/65 |

FOREIGN PATENT DOCUMENTS

| | | |
|---|---|---|
| JP | 33-10100 | 11/1958 |
| JP | 52-18073 | 4/1977 |
| JP | 59-75 | 1/1984 |
| JP | 6-502330 | 3/1994 |
| JP | 8-504347 | 5/1996 |
| JP | 10-99456 | 4/1998 |
| JP | 11-169469 | 6/1999 |
| JP | 2000-167072 | 6/2000 |
| JP | 2002-253687 | 9/2002 |

OTHER PUBLICATIONS

Takehiro Nishidai, "Radiotherapy physics", Bunkodo, Feb. 26, 2001, pp. 95-153.
Masahiro Hiraoka et al., "Radiotherapy Manual", Chugai-Igakusha, Apr. 10, 2001, pp. 19-63.
Kenji Hara et al., U.S. Appl. No. 11/152,504, filed Jun. 25, 2005, "Radiotherapy Apparatus and Operating Method of the Same", (Image File Wrapper available).

* cited by examiner

*Primary Examiner*—Edward J. Glick
*Assistant Examiner*—Anastasia S. Midkiff
(74) *Attorney, Agent, or Firm*—Wenderoth, Lind & Ponack, L.L.P.

(57) ABSTRACT

A radiotherapy apparatus includes an irradiation head section, an X-ray source section and a sensor array section. The irradiation head section irradiates therapeutic radiation to a therapeutic field of a target substance. The X-ray source section irradiates diagnostic X-rays to the therapeutic field of the target subject. The sensor array section detects the diagnostic X-rays which have transmitted the target subject, and outputs diagnostic X-ray image data based on the detected diagnostic X-rays. The sensor array section moves in conjunction with movement of the irradiation head section.

14 Claims, 21 Drawing Sheets

DIRECTION OF X-RAY BEAM

RADIOTHERAPY APPARATUS
MONITORING THERAPEUTIC FIELD IN
REAL-TIME DURING TREATMENT

BACKGROUND OF THE INVENTION

1. Field of the Invention

The present invention relates to a radiotherapy apparatus and more specifically to a radiotherapy apparatus used for stereotactic radiotherapy.

2. Description of the Related Art

A radiotherapy apparatus for treating cancers and tumors using radiation is known. As a 3-dimensional irradiation radiotherapy apparatus which irradiates stereotactic multi-path radiotherapy apparatus, radio-surgery therapy apparatus, lineac (medical linear accelerator) therapy apparatus, and others are known in "Radiotherapy physics", by Takehiro Nishidai, (Bunkodo, Feb. 26, 2001, pp. 95–153) and "Radiotherapy Manual", by Masahiro Hiraoka, Keishi Sasai, and Toshihiko Inoue, (Chugai-Igakusha, Apr. 10, 2001, pp. 19–63).

Now, stereotactic multi-path irradiation is radiotherapy to irradiate radiation concentratedly to a small seat of disease from multi-directions to achieve radiotherapy effects, and at the same time, to hold the exposure dose of the surrounding tissues to the minimum. The therapy indicates its greatest force in radiotherapy of primary benign brain tumors, solitary metastatic brain tumors not larger than 3 cm in size, minor lesion in a brain such as skull base metastasis which is difficult to operate, or arterial malformation or venous maloperation, and others.

The radiosurgery therapy apparatus irradiates thin radiation beams to a predetermined small area from one or multiple radiation irradiation units fixed to therapy apparatus. As radiation irradiating units, a gamma ray source or lineac is used. In the radiosurgery therapy apparatus, the diseased part of a patient such as skull or the peripheral regions are mechanically fixed by using a precision positioning/diseased part fixing jig, which is a fixing tool for stereotactic radiation irradiation. This frame is used as a coordinate reference jig for positioning, and diagnostic images are obtained using X-ray CT (computed tomography), MRI, and the like, and the exact position and shape of the diseased part are deduced. The patient is mechanically fixed as-framed to an irradiation apparatus which includes one or multiple radiation irradiation units and a collimater mechanism that collimates and concentrates the therapeutic radiation to a small region. By this, the radiation field is accurately adjusted to the small region mechanically, and precise stereotactic irradiation is carried out. In the radiosurgery therapy apparatus, radiation (X-ray) for radiotherapy is irradiated based on the diagnostic images filmed in advance. That is, a diagnostic X-ray system for observation of the diseased part in real time (X-ray generating unit—image detector) is not provided, and the radiation is never irradiated while observing the diseased part in real time.

In the lineac therapy apparatus, isocentric radiotherapy is carried out by rotating a large-size gantry 360 degrees around an axis parallel to the installation surface. In addition to this, by adding vertical movement, 2-dimensional movement in horizontal planes and rotation in the same horizontal plane of the therapeutic bed, diversified irradiations are enabled. In the lineac therapy apparatus, high-speed position control is not possible. Consequently, real-time follow-up irradiation to a therapeutic field which moves at a high speed as movement due to heart pulses is not possible. In addition, as a monitoring section of a radiation field under irradiation, linacgraphy of transmitted radiation of the therapeutic X-rays is used. Because the therapeutic X-ray provides strong permeability and has many scattering radiations, the picture quality for real-time monitor of the radiation field is not superior. In the lineac therapy apparatus, there is a method for following markers mounted to the diseased part by the diagnostic X-ray system, estimating the position of the diseased part, and irradiating the radiation when the estimated position overlaps the radiation field (body-in-motion tracking irradiation). Now, the diagnostic X-ray system includes a diagnostic X-ray generating unit mounted to the ceiling and an image detector mounted to the lower part of the lineac therapy apparatus. In this method, it is not practiced to grasp the position of the actual diseased part in real-time and to irradiate radiation to it while tracking in such a manner that the actual position of the diseased part overlaps the radiation field. Because the X-ray generating unit is fixed to the ceiling, the distance with the image detector is large. In addition, there is a case that the image detector enters the shadow of a main body of the lineac therapy apparatus, so that the diagnostic X-ray from the X-ray generating unit may not reach the image detector. To cope with it, a slightly larger number of X-ray generating units are mounted to the ceiling, and two usable ones are selected to use. Furthermore, the image detector is installed in the region to which transmission X-ray (the therapeutic X-ray that penetrated the diseased part) and scattering X-ray (the therapeutic X-ray that are scattered in the diseased part) are directed.

In conjunction with the above description, stereotactic surgical apparatuses and methods are disclosed in PCT International Patent Applications (International Application Nos. PCT/US91/07696, and PCT/US93/11872).

One of these stereotactic surgical apparatuses is an apparatus which isocentrically drives electronic therapeutic X-ray lineac, and the electronic lineac is provided to a tip section of a general-purpose industrial robot arm. This apparatus essentially achieves non-isocentric irradiation therapy by free moving capabilities of the robot arm with six degrees of freedom. The exact shape and position of the diseased part are determined by X-ray CT and/or MRI in advance and are inferred by relating them to landmark body tissue such as the skull and the breast and markers embedded in or in the vicinity of the diseased part (e.g., a small-size gold plate embedded in the diseased part). The therapeutic X-ray is precisely irradiated while the stereotactic surgical apparatus monitors the movement of the landmark by the two diagnostic X-ray systems with different visual lines at the time of the therapeutic irradiation, and corrects the sight of the therapeutic X-ray. It takes 1 to 2 seconds to correct the sight and 0.5 to 1 second for irradiation time. Of these two diagnostic X-ray systems, the X-ray generating unit is firmly secured to the ceiling. The image receiver (image detector) that receives the transmitted X-ray is disposed to the lower part of the bed. That is, the X-ray generating unit is located considerably distant from the image detector. In addition, due to the rotation of the lineac therapy apparatus, the image detector enters the shade of the apparatus and diagnostic X-rays from the X-ray generating unit may not reach the image detector. On the other hand, the image receiver is located on the opposite side to the therapeutic X-ray irradiating apparatus with respect to the bed. That is, the image receiver is installed in a region where transmitted X-ray or scattered X-ray are directed.

The other of the above stereotactic surgical apparatuses is an apparatus that drives the electronic lineac along the gantry, and two diagnostic X-ray systems (X-ray generating unit-image receiver) and an electronic lineac are provided to the gantry. By allowing the electronic lineac to rotate not only around one axis in the horizontal direction but also around one axis in the vertical direction, three-dimensional irradiation can be achieved. However, the irradiation system is isocentric. In this stereotactic surgical apparatus, too, the exact shape and position of the diseased part are determined by means such as the X-ray CT are inferred by relating them to the landmark body tissues or the markers embedded in or in the vicinity of the diseased part. The therapeutic beams are precisely irradiated while the stereotactic surgical apparatus monitors the movement of the landmark by using the two diagnostic X-ray systems with different visual lines at the time of the therapeutic irradiation, and corrects the sight of the beam. It takes 1 to 2 seconds for time to correct the sight and 0.5 to 1 second for irradiation time.

These two diagnostic X-ray systems are installed on the gantry to which the electronic lineac is installed. In the same manner, the X-ray generating unit is installed on the gantry on the electronic lineac side distant from the electronic lineac. In addition, the image receiver is located on the gantry on the opposite side of the X-ray generating unit with respect to the diseased part. That is, the image receiver is installed in the region where transmitted or scattering beams are directed.

In general, the diseased part of a patient moves even during radiotherapy. In particular, in a diseased part below the neck, an irradiation subject such as a tumor is constantly moving due to the movements and state of organs such as breathing, heart pulses, vermiculation, and urine volume in a bladder. For example, when the patient lies down only, the body gradually becomes flat. In addition, though breathing and heart pulses are cyclic movements, movements of organs associated with them do not always pass the same route every time.

The movement of the irradiated subject is intended to be accurately caught in real time, and the heart pulse, which is one of the quickest movements, is 1 to 2 times/sec. Consequently, in order to obtain accurate tracking of the movement in real time, it is said that a technique to obtain diagnostic images at about 30 images per second is required. If the irradiated subject is accurately tracked in real time and radiation is irradiated, it is necessary to direct the radiation irradiating head accurately to the irradiated subject every 1/30 second. In addition, in order to obtain a high-quality diagnostic image for tracking, it is important to eliminate the effect of the therapeutic radiation (X-rays) to the image detector of the diagnostic X-ray system.

SUMMARY OF THE INVENTION

Therefore, it is an object of the present invention to provide a radiotherapy apparatus that can monitor a therapeutic field state in real time even during radiation irradiating radiotherapy.

Another object of the present invention is to provide a radiotherapy apparatus that can eliminate influence of therapeutic radiation (X-ray) on an image detector of a diagnostic X-ray system.

Still another object of the present invention is to provide a radiotherapy apparatus that can irradiate radiation to a therapeutic field while tracking the therapeutic field even when the therapeutic field moves during radiotherapy.

It is a further object of the present invention to provide a radiotherapy apparatus that can quickly adjust a sight from a wide range of region in addition to irradiation around one-rotation axis or isocentric irradiation.

Another object of the present invention is to provide a radiotherapy apparatus that can precisely irradiate radiation to a diseased part while alleviating burdens on a patient, resulting in improvement of therapeutic effects.

In an aspect of the present invention, a radiotherapy apparatus includes an irradiation head section, an X-ray source section and a sensor array section. The irradiation head section irradiates therapeutic radiation to a therapeutic field of a target substance. The X-ray source section irradiates diagnostic X-rays to the therapeutic field of the target subject. The sensor array section detects the diagnostic X-rays which have transmitted the target subject, and outputs diagnostic X-ray image data based on the detected diagnostic X-rays. The sensor array section moves in conjunction with movement of the irradiation head section.

Here, the X-ray source section preferably moves in conjunction with the movement of the sensor array section.

Also, the sensor array section is preferably provided in a vicinity of the irradiation head section. In this case, the sensor array section preferably includes sensor arrays provided on both sides of the irradiation head section.

Also, it is preferable that a distance between each of the X-ray source section and the sensor array section and an isocenter is smaller than a distance between the irradiation head and the isocenter.

Also, the X-ray source section and the sensor array section are preferably provided at positions symmetrical to each other with respect to the isocenter.

Also, it is preferable that the irradiation head section is movably provided for any one of a C-type gantry and a Ω type gantry, which have a rail track on which the irradiation head section moves, and an L type gantry and a robot arm, which move with the irradiation head section held.

Also, it is preferable that the irradiation head section is movably provided to an O-type gantry, which has a rail track on which the irradiation head section moves. In this case, the X-ray source section and the sensor array section are preferably provided inside a ring of the O-type gantry.

Also, the radiotherapy apparatus may further include a control unit, an image processing unit and a head swing mechanism. The image processing unit generates diagnostic images of the therapeutic field based on the diagnostic X-ray image data. The head swing mechanism swings the irradiation head section such that the therapeutic radiation outputted from the irradiation head section follows the movement of the therapeutic field. The irradiation head section is movably coupled to the O-type gantry. The control unit carries out position control of the head swing mechanism based on the diagnostic images, a position of the irradiation head section, and a swing state of the irradiation head section, such that the irradiated field of the irradiation head section tracks the therapeutic field, and controls the irradiation head section to irradiate the therapeutic radiation after the position control of the head swing mechanism. In this case, the control unit may calculate a first coordinate as a coordinate of the therapeutic field in the diagnostic images based on a predetermined image pattern indicating the therapeutic field on the diagnostic images, calculate a second coordinate as a coordinate of the irradiated field based on the position of the radiation head section and the swing state of the irradiation head section, and carry out the positional control of the head swing mechanism such that the therapeutic field is contained in the irradiated field based on the first and second coordinates. In this case, the control unit may carry out the position control of the head swing mechanism and the control of the irradiation head section for every predetermined time period. Also, the head swing mechanism swings the irradiation head section around two axes orthogonal to each other.

Also, the radiotherapy apparatus may further include a head circumferential moving mechanism configured to move the irradiation head section along a ring of the O-type gantry.

Also, the radiotherapy apparatus may further include a gantry rotating mechanism configured to rotate the O-type gantry around a vertical axis.

Also, the radiotherapy apparatus may further include a microwave generating unit configured to generate microwaves and a waveguide configured to couple the microwave generating unit and the irradiation head section and to guide the microwaves from the microwave generating unit to the irradiation head section. In this case, the microwave belongs to a C band, and the irradiation head section comprises an accelerator tube configured to accelerate electrons of an electron beam with the microwave. Also, the microwave belongs to an X band, and the irradiation head section comprises an accelerator tube configured to accelerate electrons of an electron beam with the microwave.

DESCRIPTION OF THE PREFERRED EMBODIMENTS

Hereinafter, a radiotherapy apparatus according to the present invention will be described in detail with reference to the attached drawings.

First Embodiment

Figure 1:
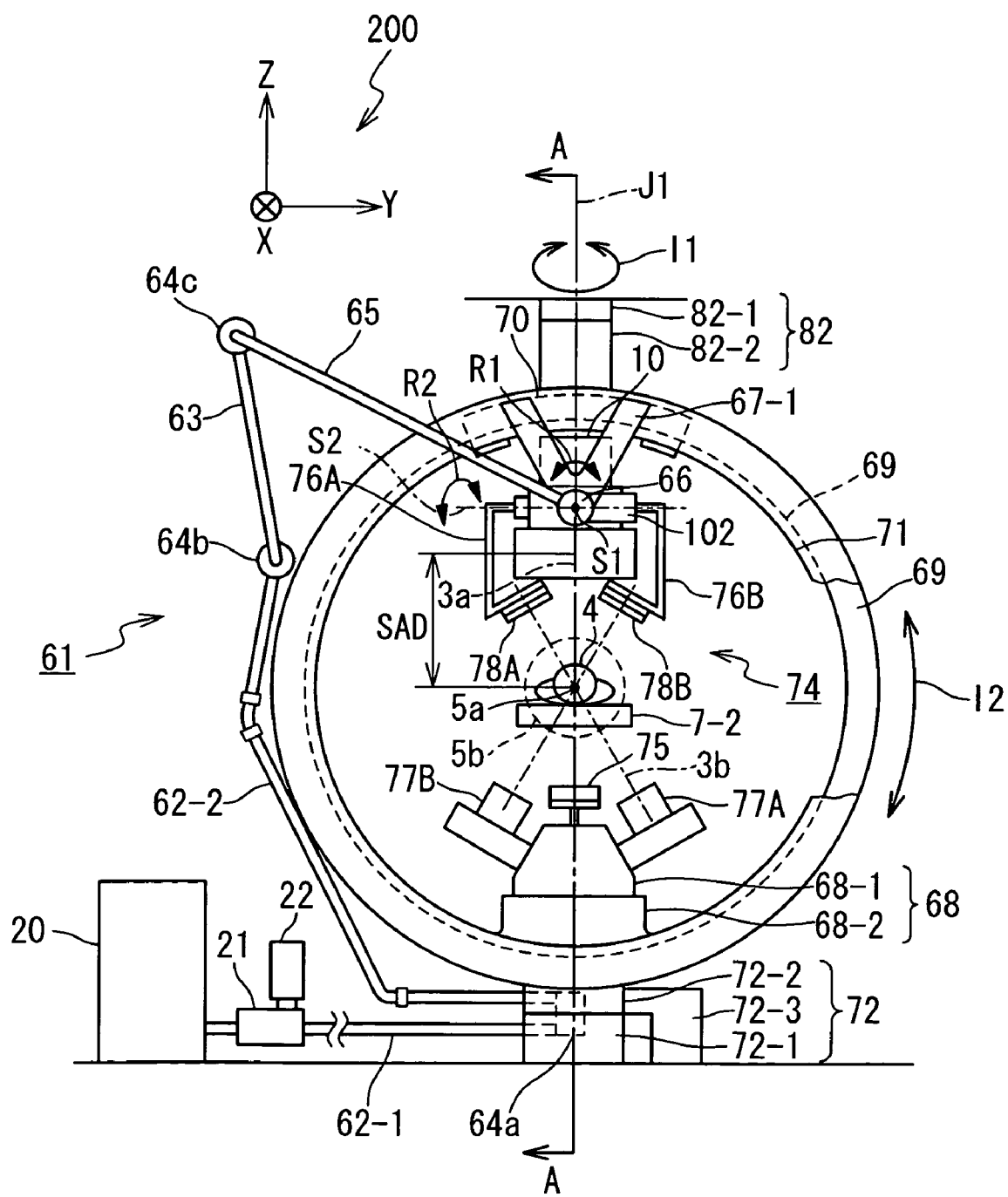
FIG. 1 is a front view showing the configuration of a radiotherapy apparatus according to a first embodiment of the present invention.
Figure 2:
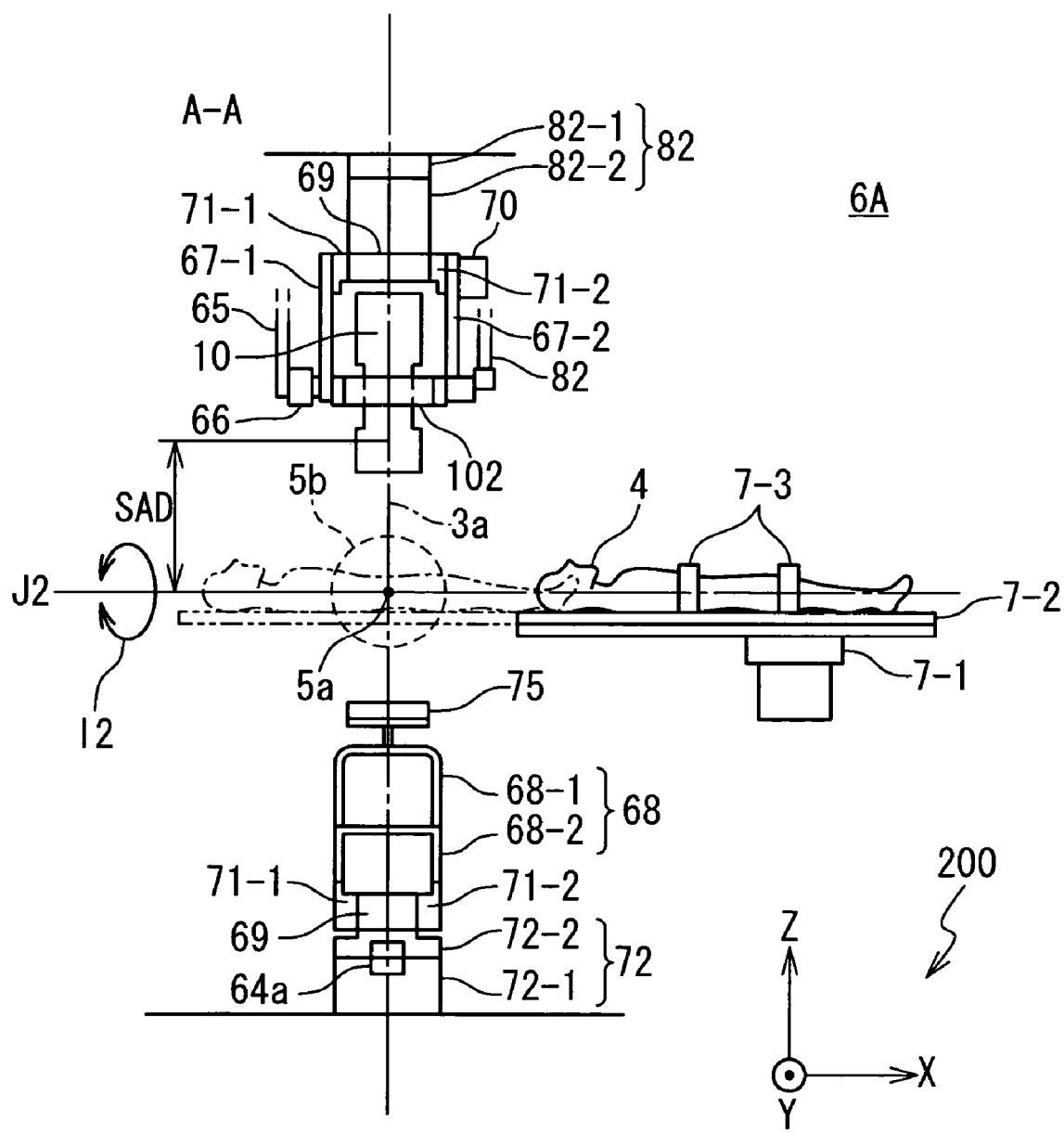
FIG. 2 is a cross sectional side view showing the configuration of the radiotherapy apparatus according to the first embodiment of the present invention.

The radiotherapy apparatus according to the first embodiment of the present invention will be described. FIGS. 1 and 2 are a front view and a cross sectional side view showing the structure of the radiotherapy apparatus according to the first embodiment of the present invention. In the drawings, a part of the structure of the radiotherapy apparatus is omitted. Coordinate axes 200 indicate a three-dimensional orthogonal coordinate system which has X-axis, Y-axis, and Z-axis in FIG. 1 and FIG. 2.

A radiotherapy apparatus 6A includes a therapeutic bed system 7, an X-ray head 10, a support frame 67-1, a support frame 67-2, an O-type gantry 69, a movement following type waveguide tube system 61, a microwave generating unit 20, and a real-time imager 74.

The therapeutic bed system 7 includes a bed driving system 7-1, a therapeutic bed 7-2, and a patient fixing apparatus 7-3. The therapeutic bed 7-2 is loaded with a patient 4 who undergoes radiotherapy, and is moved to a specific position in the apparatus 6A. The patient fixing apparatus 7-3 fixes the patient 4 to the therapeutic bed 7-2. The bed driving system 7-1 can move the therapeutic bed 7-2 in three-axial directions of X-axis, Y-axis, and Z-axis. The bed driving system 7-1 can adjust the position of the therapeutic bed 7-2 so that the diseased part 5 as a therapeutic field is located at an isocenter 5a based on photographed image data from the real-time imager 74 under the control of a system control unit 80 to be described later. For the therapeutic bed 7-2 and the patient fixing apparatus 7-3, material and shape are selected in such a manner that are suited for the use of an image diagnosis apparatus as the real-time imager 74.

The O-type gantry 69 includes a ring circumferential moving mechanism 70, O-type driving rings 71-1 and 71-2, a gantry rotating mechanism 72, and an upper support mechanism 82. The O-type gantry 69 (main body) is installed to surround the periphery of the therapeutic bed 7-2, and is composed of a pipe with a rectangular cross section and formed in a circular ring. The O-type gantry 69 is installed on the gantry rotating mechanism 72 to be upright with respect to the horizontal plane (XY plane). The therapeutic bed 7-2 and the X-ray head 10 are disposed so that the circle center comes to the isocenter 5a.

The gantry rotating mechanism 72 includes a foundation section 72-1, a rotating section 72-2, and a driving section 72-3. The foundation section 72-1 is fixedly installed to a bottom surface (a floor surface, etc.). The rotating section 72-2 is rotatably installed on the foundation section 72-1, and fixedly holds the O-type gantry 69. The driving section 72-3 rotates the rotating section 72-2 and the O-type gantry on it. That is, around a first rotating axis J1 as an axis in the vertical direction (Z-axis direction), the O-type gantry 69 is rotated as shown by I1 in FIG. 1. In this case, the first rotating axis J1 overlaps the diameter of a circle of the O-type gantry 69 and passes the circle center as the isocenter 5a.

The O-type drive rings 71-1 and 71-2 are rings which have inside diameters and outside diameters similar to those of the O-type gantry 69. The O-type drive rings 71-1 and 71-2 are rotatably provided to the O-type gantry 69 in a concentric manner and parallel manner to the circle of the O-type gantry 69 to put the O-type gantry 69 therebetween. The O-type drive rings 71-1 and 71-2 rotate to the O-type gantry 69 around a second rotating axis J2 which is perpendicular to the plane of the O-type gantry 69 and which is perpendicular to the first rotating axis J1 and passes the isocenter 5a, as shown by 12 in FIG. 1. At this time, the O-type drive rings 71-1 and 71-2 rotate integrally with the ring circumferential moving mechanism 70.

The ring circumferential moving mechanism 70 is movably connected with the O-type gantry 69 and fixedly with the O-type drive rings 71-1 and 71-2. Thus, the mechanism 70 moves the O-type drive rings 71-1 and 71-2 along the O-type gantry 69 in the circumferential direction as shown by 12 in FIG. 1. The ring circumferential moving mechanism 70 may include the O-type drive rings 71-1 and 71-2. A rack and pinion system, belt system, and the like may be adopted for the ring circumferential moving mechanism 70.

The upper support mechanism 82 has a foundation section 82-1 and a rotating section 82-2. The foundation section 82-1 is fixedly installed to an upper section (ceiling, etc.). The rotating section 82-2 is rotatably installed below the foundation section 82-1 and holds the O-type gantry 69 from the above direction. That is, the rotating section 82-2 supports the rotation of the gantry rotating mechanism 72 around the first rotating axis J1 in the top section of the O-type gantry 69.

The O-type gantry 69 can rotate for 160 degrees around the first rotating axis J1. In addition, the O-type drive rings 71-1 and 71-2 can rotate for 360 degrees on the O-type gantry 69. That is, the sections such as an X-ray head 10 to be described later fixed to the O-type drive rings 71-1 and 71-2 are moved in such a manner as to draw an ⅝ sphere (⅝ spherical shell) with the isocenter 5a as a center. The O-type gantry 69, the ring circumferential moving mechanism 70, the O-type drive rings 71-1 and 71-2, and the gantry rotating mechanism 73 are formed of material with a large rigidity, for example, stainless steel. The O-type gantry 69 (main body) is 200–400 mm wide, 100–200 mm thick, and 1200–2000 mm in radius from the isocenter 5a.

The X-ray head 10 is a radiation irradiating head which irradiates the therapeutic X-rays 3a to a radiation field 5' (diseased part 5). The X-ray head 10 has a small-size electron lineac which irradiates the therapeutic X-rays 3a. The X-ray head 10 is movably installed to the O-type gantry 69 via the O-type drive ring 71, the support frame 67-1 to be described later and a support frame 67-2 to be described later. The X-ray head 10 has a support frame 102.

The support frame 102 includes a first swing mechanism 131 and a second swing mechanism 132. The first swing mechanism 131 is a mechanism to vibrate or turn the X-ray head 10 around a first swing axis S1 on the O-type gantry 69 as shown by R1 in FIG. 1. The first swing axis S1 is provided on the axis that nearly passes the inertia center of the X-ray head 10 or in the vicinity of it so that the inertia becomes small when the X-ray head 10 is swung. The second swing mechanism 132 is a mechanism to oscillate or turn the X-ray head 10 around the second swing axis S2 on the O-type gantry 69 as shown in by R2 in FIG. 1. The second swing axis S2 is provided on the axis that nearly passes the inertia center of the X-ray head 10 or in the vicinity of it so that the inertia becomes small when the X-ray head 10 is swung. The detail will be discussed later.

Also, a sensor array 78A and a sensor array 78B are fixedly held by a holding frame 76A and a holding frame 76B. The support frame 67-1 is fixedly connected to the O-type drive ring 71-1 on one side and to the support frame 102 on the other side. The support frame 67-2 is fixedly connected to O-type drive ring 71-2 on one side and to a portion opposite to a connection between the support frame 102 and the support frame 67-1 in the support frame 102 on the other side. That is, the support frame 67-1 and the support frame 67-2 hold the X-ray head 10 on the inner circumferential side of the O-type gantry 69. The support frame 67-1 and the support frame 67-2 rotate together with the X-ray head 10 held by the support frame 102 in accordance with the rotation of the O-type drive rings 71-1 and 71-2 by the ring circumferential moving mechanism 70.

The real-time imager 74 (sensor arrays 78A and 78B) detects images of the diagnostic X-rays 3b which have transmitted the patient 4 when the diagnostic X-ray 3b as a weak fan beam X-ray is irradiated to the therapeutic field of the patient 4 from the two directions (X-ray sources 77A and 77B). An image processing is carried out on the detected images by an image processing unit 31 and a 3-dimensional tomography image of the therapeutic field or diseased part 5 is displayed on a computer screen. The real-time imager 74 is controlled by a system control unit 80. The real-time imager 74 includes 2 sets of the X-ray sources 77A and 77B and the sensor arrays 78A and 78B like usual x-ray cameras, a holding section 68 that holds the X-ray sources 77A and 77B, and holding frames 76A and 76B that hold the sensor arrays 78A and 78B. The holding section 68 (68-1 and 68-2) is fixedly held to O-type drive rings 71-1 and 71-2 on one side. Also, the other side thereof is held to have the X-ray sources 77A and 77B on both sides, and to aim at the isocenter 5a while sandwiching a plane formed from the first rotating axis J1 and the second rotating axis J2. Furthermore, the holding section 68 has a protection plate 75 at the top to absorb the therapeutic X-ray 3a penetrating the patient 4. The X-ray sources 77A and 77B are moved in conjunction with the motion of the X-ray head 10 (motion of the O-type drive rings 71-1 and 71-2).

The holding frame 76A has one end extending downward from one side surface of the X-ray head 10 (holding frame 102). The sensor array 78A is connected to the other end of the frame 76a. Similarly, the holding frame 76B has one end extending downward from one side surface of the X-ray head 10 (holding frame 102). The sensor array 78B is connected to the other end of the frame 76B. The X-ray source 77A and the X-ray source 77B are mounted to the holding section 68. The two sources are located on the positions opposite to each other while putting the plane formed from the first rotating axis J1 and the second rotating axis J2 therebetween. The sensor array 78A and the sensor array 78B are similar to the sources. Because the diagnostic images are obtained by irradiating the diagnostic X-rays 3b from two directions, the motion of each portion of the body of the patient 4 can be quickly and accurately grasped. Also, the real-time imager 74, the O-type drive rings 71-1 and 71-2, and the O-type gantry 69 are mechanically and tightly connected and have a common coordinate reference.

The sensor array 78A is mounted to one end of the holding frame 76A. The sensor array 78A is located near the X-ray head 10 but is disposed with care to prevent the sensor array 78A from interfering with the course of the therapeutic X-ray 3a which is irradiated from the X-ray head 10. Therefore, the sensor array 78A does not receive the strong X-rays from the X-ray head 10. The perpendicular line from the center portion of the light-receiving surface of the sensor is directed to the isocenter 5a, and the X-ray source 77A is disposed on the extension line. Similarly, the sensor array 78B is mounted on one end of the holding frame 76B. The sensor array 78B is located near the X-ray head 10 but is disposed with care to prevent it from interfering with the course of the therapeutic X-ray 3a which is irradiated from the X-ray head 10. Therefore, the sensor array 78B does not receive strong X-rays from the X-ray head 10. The perpendicular line from the center portion of the light-receiving surface of the sensor is directed to the isocenter 5a, and the X-ray source 77B is disposed on the extension line.

The sensor arrays 78A and 78B receive the diagnostic X-ray 3b which penetrates the patient 4. The sensor arrays 78A and 78B are fixedly disposed on the circumference of a circle with the isocenter 5a as the center, and the isocenter 5a surrounds the diagnostic space to which the patient 4 is located. Each sensor array 78A or 78B is provided with a large number of super high-sensitivity CdTe sensors, and has 0.5 mm resolution. Also, the irradiation time of diagnostic X-ray 3b is 0.0025 to 0.01 seconds per shot.

The distance between each of the X-ray sources 77A and 77B and the sensor array 78A and 78B and the isocenter 5a is smaller than the distance between the X-ray head 10 and the isocenter 5a. That is, since the X-ray source and the sensor array are located close to the patient 5, the image quality of the diagnostic image is improved. In addition, it is possible to secure a wide movable range of the X-ray head 10 on the O-type gantry 69. It is preferable that the angle between the perpendicular line that passes the isocenter 5a from the center part of the sensor array 78A surface and the perpendicular line that passes the isocenter 5a from the center part of the sensor array 78B surface is between 20 degrees and 90 degrees, and more preferably, between 40 degrees and 60 degrees. This is determined on the basis of the condition in which the X-ray head 10, the X-ray source 77A and the X-ray source 77B correctly operate without affecting one another and diagnostic images with sufficient accuracy are obtained.

The output side of the X-ray generation control apparatus of the real-time imager 74 is connected with the power supply and anodes, cathodes, and grid electrodes of the X-ray sources 77A and 77B. When an X-ray generation command signal is outputted from the system control unit 80 to the X-ray generation control apparatus, the X-ray generation control apparatus supplies the power supply to an electron gun driving circuit. In response to this, electron beams are emitted from the cathodes of the X-ray sources 77A and 77B, and a negative bias voltage applied to the grid electrodes is released to a zero potential. Thus, the electron beam passes the holes of the grid electrode and is supplied to the anode. When the electron beam reaches the anode, secondary X-rays are generated from the anode and fan-shaped diagnostic X-ray 3b is irradiated towards the patient 4 via a collimator mounted to a window.

The transmission X-ray detected by the sensor arrays 78A and 78B are converted into current signals proportional to the transmitted X-ray dosage, and the current signals are sent to an image signal digitizer and a data recorder via a pre-amplifier and a main amplifier, and recorded as diagnostic image data. The photographing, data recording, and other processes of using the diagnostic X-ray 3b are controlled by the system control unit 80. The recorded diagnostic image data is outputted from the data recorder to the image processing unit 31 to be described later, and is subject to data processing by the image processing unit 31. The processed data is reproduced and displayed on a display unit of the system control unit 80 as a diagnostic image of the diseased part 5.

Through the above-mentioned 3-axis drives (I1, I2), an isocentric motion of the X-ray head 10 on the ⅝ spherical shell with the isocenter 5a as a center becomes possible and the X-ray head 10 is directed to the isocenter 5a. Further, through the above-mentioned 2-axis drives (R1, R2), a pseudo-nonisocentric motion of the X-ray head 10 on the ⅝ spherical shell becomes possible and the X-ray head 10 is directed to a desired point in a 3-dimensional region 5b in the surrounding vicinity of the isocenter 5a, as shown in FIG. 1. This pseudo-nonisocentric motion is a swing movement around the inertia center of the X-ray head 10. Therefore, a markedly quick motion can be carried out, as compared to the isocentric motion. By the pseudo-nonisocentric high-responsive quick tracking motion, for example, it is possible to make the head sights to track quick movements such as heart pulses with a high speed response and precisely.

The microwave generating unit 20 includes a klystron (not shown) and generates microwaves by a klystron system. The microwave generating unit 20 has a circulator 21 and a dummy load 22 related to the waveguide, and supplies electron acceleration microwaves to the X-ray head 10 via the waveguide tube system 61. Here, C-band (5.6 GHz) microwaves are supplied. The microwave generating unit 20 is controlled by the system control unit 80. The waveguide tube system 61 is a waveguide to supply the microwave generated by the microwave generating unit 20 to the X-ray head 10. The waveguide tube system couples a link arm 62-1, an articulation 64a, a link arm 62-2, an articulation 64b, a link arm 63, an articulation 64c, a link arm 65, an articulation 66, and the X-ray head 10 to one another to form a link mechanism. The articulation 64a can rotate around an axis in the first rotating axis J1 direction, and the articulations 64b and 64c and the articulation 66 can rotate around an axis in the second rotating axis J2 direction. By the way, the X-ray head 10 at the link head slides along the O-type gantry 69 with the motion of the O-type drive ring 71-1 and is swung around the articulation 66 by the first swing mechanism 131. The articulations 64a, 64b, 64c, and 66 include a rotary RF coupler 50 to be described later, which transfers microwaves through axial rotation. The link arms 62-1, 62-2, 63, and 65 include a waveguide tube 51 to be described later and electromagnetically communicate through articulations 64a through 64c, and 66. The microwaves generated by the microwave generating unit 20 are supplied to the X-ray head 10 via the articulation 64a—the link arm 62—the articulation 64b—the link arm 63—the articulation 64c—the link arm 65- and the articulation 66.

SAD (Source Axis Distance) shown in FIG. 1 is equivalent to the distance from the isocenter 5a to the target 121 to be described later in the X-ray head 10. In this embodiment, the SAD as a reference is set to 80 to 100 cm.

Figure 3:
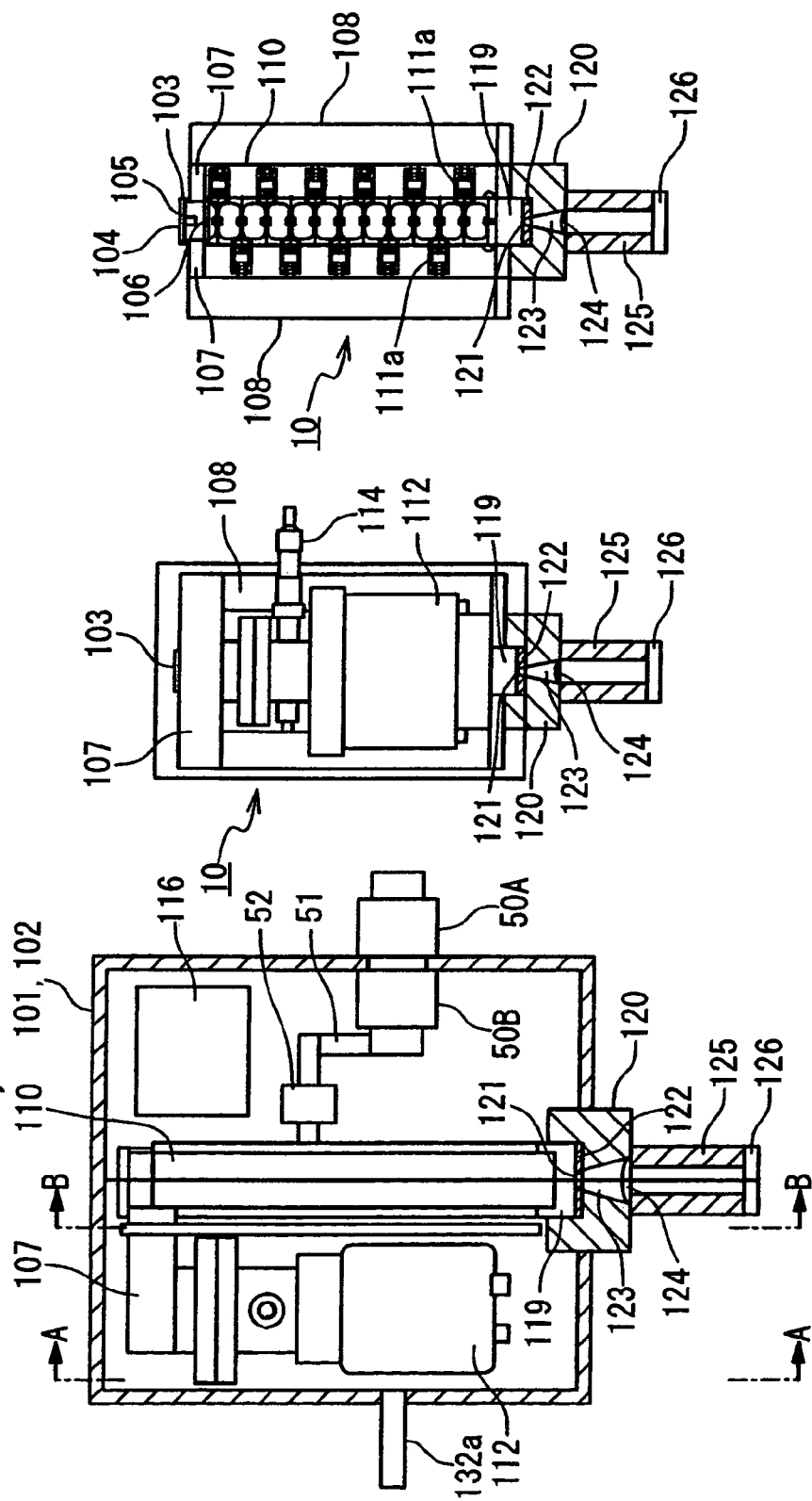
FIG. 3A is a diagram showing the configuration of an X-ray head applied to the radiotherapy apparatus according to the present invention.
FIG. 3B is a cross sectional view along line AA in FIG. 3A.
FIG. 3C is a cross sectional view along line BB in FIG. 3A.

The X-ray head 10 will be described in detail below with reference to FIGS. 3A to 3C and FIG. 4. FIG. 3A is a diagram showing the configuration of the X-ray head applied to the radiotherapy apparatus according to the present invention. FIG. 3B is a cross sectional view along the line AA in FIG. 3A, and FIG. 3C is a cross sectional view along the line BB in FIG. 3A.

The X-ray head 10 has a small-size electron lineac which generates the therapeutic X-ray 3a in an energy range of 4 MeV to 10 MeV. The X-ray head 10 is movably supported to the O-type gantry 69 via a support frame 102. At the same time, the X-ray head 10 is swingably coupled to the articulation 66 (rotary RF coupler) of the waveguide tube system 61.

The X-ray head 10 has a main body section of the X-ray head 10 covered with a head cover 101 and is provided with a radiating section 120 for emitting radiation to the tip section of the main body section. In the head cover 101 that covers the head main body, an electric circuit/cooling water circuit 116, an accelerator tube 110, a RF window 52, a waveguide tube 51, part of a rotary RF coupler 50B, an exhaust pipe 107, an ion pump 112, a target exhaust chamber 119, a target 121, and a cooling plate 122 are provided.

A cable (not shown) connected to the external power supply (not shown) is introduced from an insulation glass 103 at the tail end of the accelerator tube 110 into the head cover 101, and is connected to a cathode 105 of an electron gun 104. An anode 106 is disposed face to face with this cathode 105. The power supply of the electron gun 104 is controlled by the system control unit 80. Gas between the cathode 105 and the anode 106 is discharged by an exhaust pipe 107 for communication of the ion pump 112. The space from which gas is discharged is connected from the electron gun 104 to the accelerator tube 110, and further from the accelerator tube 110 to the radiating section 120. Because the ion pump 112 is directly connected to the acceleration pipe 110, the vacuum of the accelerator tube 110 can be kept constantly at a high vacuum, and can stably accelerate the electron beams. Thus, the therapeutic X-ray 3a can be stably outputted. The distance from the insulation glass 103 to the tip section of the accelerator tube 110 is about 360 mm. This size is smaller to about ⅓ that of a conventionally used accelerator tube. At the same time, the weight is reduced, too. This is accomplished by using high frequency (high energy) microwaves of C band (5.6 GHz) in place of the conventionally used S band microwaves.

Figure 4:
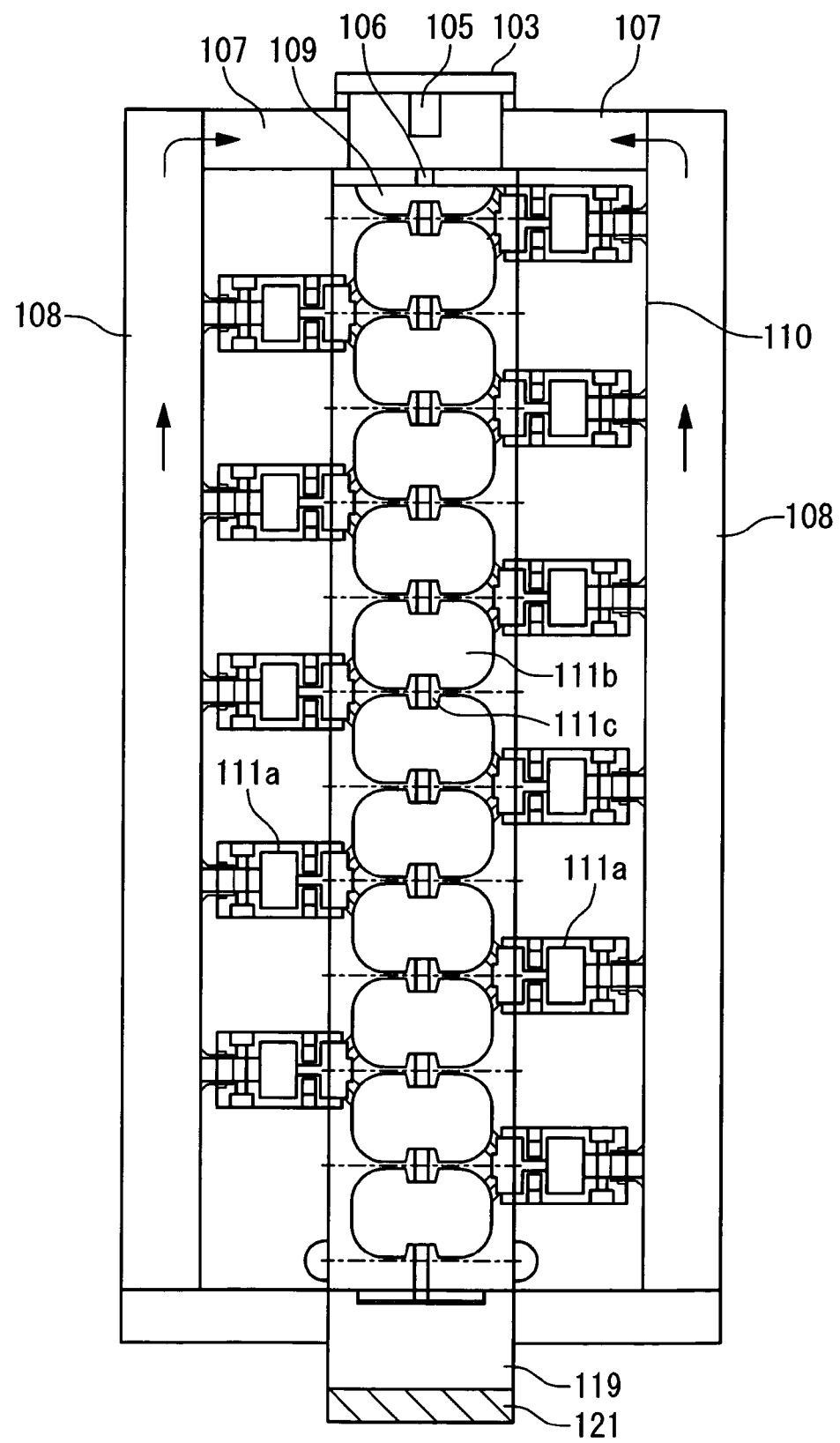
FIG. 4 is an enlarged view of the vicinity of an electron gun and accelerator tube of FIG. 3C.

FIG. 4 is an enlarged view of the vicinity of the electron gun 104 and the accelerator tube 110 of FIG. 3C. The center hole of the anode 106 of the electron gun 104 communicates with a buncher cavity 109 of the accelerator tube 110. Inside of the accelerator tube 110, multiple accelerator cavities 111b are connected and each of them has a center hole for an electron beam passage. The accelerator tube 110 allows the electron beam radiated from the electron gun 104 to accelerates the electron beam by microwave while passing the buncher cavity 109 and center holes 111c of the multiple accelerator cavities 111b. The accelerated electron beam collides against the X-ray target 121 as a high-energy electron beam. The accelerator cavities 111b communicate with a pair of right and left lateral exhaust pipes 108 via side couple cavities 111a, respectively. A pair of right and left lateral exhaust pipes 108 are connected to the ion pump 112 via the exhaust pipe 107 and the space in the multiple accelerator cavities 111b are under a vacuum.

Referring again to FIGS. 3A to 3C, the waveguide tube 51 communicates with the accelerator tube 110. The waveguide tube 51 communicates with the microwave generating unit 20 via a ceramic RF window 52 and rotary RF couplers 50A and 50B (through the waveguide tube system 61). The RF window 52 is an inlet to introduce microwave to the accelerator tube 110 and prevents $SF_6$ gas sealed in the waveguide tube 51 from leaking. The radiating section 120 is provided to the tip section of the main body section of the X-ray head 10 covered with the head cover 101. The radiating section is provided with the target 121, a target cooling plate 122, a primary collimator 123, and a flattening filter 124. The components from the electron gun 104 to the flattening filter 124 via the accelerator tube 110 are aligned in series along the axis of the electron beam. Thus, the accelerated electron beam passes the target exhaust chamber 119 and strikes the target 121 of the radiating section 120.

The target 121 radiates braking radiation X-rays by the incidence of high-energy accelerated electrons. The target cooling plate 122 is mounted to the target, to prevent the target from being subject to heat damage by the heat generated when braking radiation X-rays are emitted. For the target 121, a high-melting point metal such as tungsten and tantalum or their alloy is used. The primary collimator 123 is made of material such as tungsten with superior shielding capability to radiation and fewer thermal neutrons. The primary collimator reduces the X-rays from the target 121 to a specified beam width and guides to the flattening filter 124. The flattening filter 124 averages the intensity of X-rays emitted from the target 121 and produces the therapeutic X-rays 3a with a uniform dose distribution.

Furthermore, a second collimator 125 and an ionization chamber 126 for dose measurement are mounted to the tip section of the radiating section 120. The secondary collimator 125 is made of material such as tungsten with high shielding property and prevents the therapeutic X-rays 3a from transmitting. The secondary collimator 125 guides the therapeutic X-ray 3a from the flattening filter 124 to the ionization chamber 126. This secondary collimator 125 is removably attached to the end face section of the primary collimator 123. The ionization chamber 126 measures the dose of passing X-rays. The ionization chamber is mounted to the tip section of the secondary collimator 125 and gas of the specified composition is sealed. A detecting circuit (not shown) is connected to detect discharged electric charges. This detecting circuit is connected to the input side of the system control unit 80. The system control unit 80 calculates the dose of the X-rays emitted from the X-ray head 10 based on an input signal from the dose measurement ionization chamber 126, and stores it in a memory as the therapeutic dose data which the patient 4 receives.

In the radiotherapy apparatus 6 according to the present invention, the X-ray head 10 can generate the therapeutic X-ray 3a with high electron energy of 4 MeV to 10 MeV though the X-ray head 10 is as small as 500–600 mm in total length, 500 mm wide, 300 mm deep and 60–80 kg by weight. This is because the acceleration tube 110 is compact and light weight since high-frequency (high energy) C band (5.6 GHz) microwaves are used, a deflection magnet that deflects the electron beam and its related devices are not required since the accelerator tube 110 is small, and a device for generating microwaves (microwave generating unit 20) is located outside the X-ray head 10. That is, because the overall weight is reduced and the overall size is reduced, the X-ray head 10 can be moved agilely and quickly to a desired position. Also, when an accelerator tube is used which can accelerate electrons by the use of still higher-frequency X-band microwaves, the radiotherapy apparatus can be further downsized and can have its weight reduced. In such a case, the design of each unit is changed in accordance with the microwave frequency, for example, the sizes of the waveguide tube system 61, and the accelerator cavities 111$b$ of the accelerator tube 110 are changed.

Figure 5:
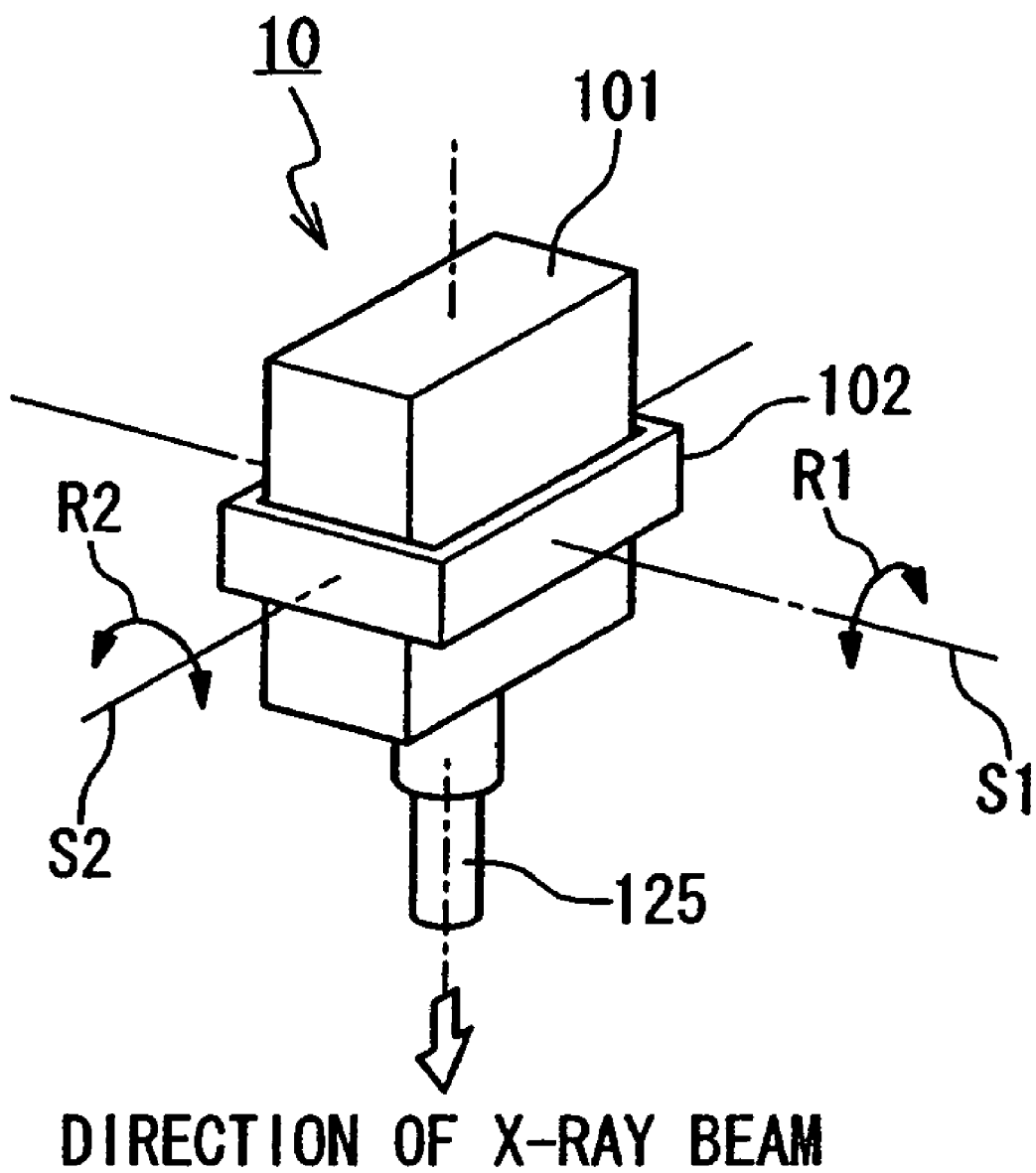
FIG. 5 is a perspective view showing an X-ray head supported on a support frame.

Next, the 2-axis swing mechanism of the X-ray head 10 will be described in detail with reference to FIGS. 5 and 6. FIG. 5 is a perspective view showing the X-ray head 10 supported by the support frame 102. As shown in FIG. 5, the head cover 101 of the X-ray head 10 is supported by the support frame 102 which has a gimbal-ring structure. The support frame 102 is mounted to a position coordinate which the first swing axis S1 and the second swing axis S2 pass including the inertia center of the X-ray head 10. The X-ray head 10 is swung around the first swing axis S1 by a first swing mechanism 131 as shown by R1 in FIG. 1, and similarly, is swung around the second swing axis S2 by the second swing mechanism 132 as shown by R2 in FIG. 1.

Figure 6A:
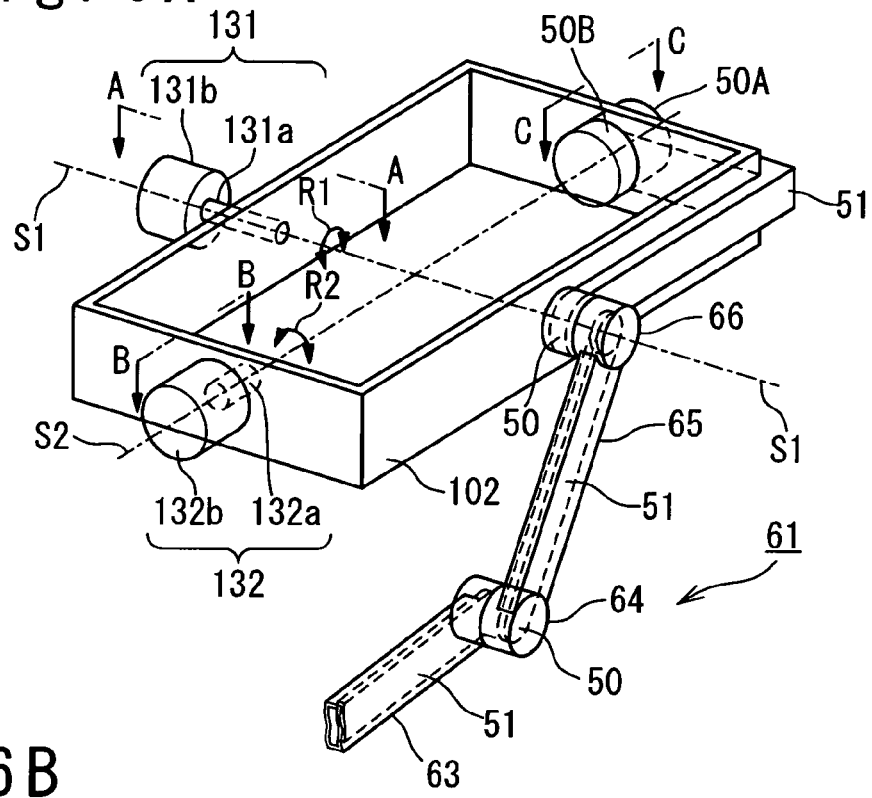
FIG. 6A is a diagram showing the configuration of the whole 2-axis swing mechanism of the support frame.

FIG. 6A is a diagram showing the configuration of the whole 2-axis swing mechanism of the support frame. FIGS. 6B to 6E are diagrams showing an S1 swing servo motor 131$b$, an articulation 66, an S2 swing servo motor 132$b$, and a pair of rotary RF couplers 50A and 50B, respectively.

Figure 6B:
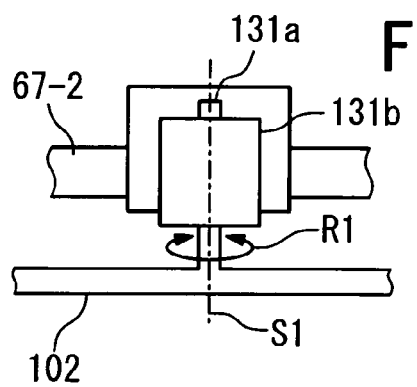
FIGS. 6B to 6E are diagrams showing an S1 swing servo motor, an articulation, an S2 swing servo motor, and a pair of rotary RF couplers, respectively.
Figure 6C:
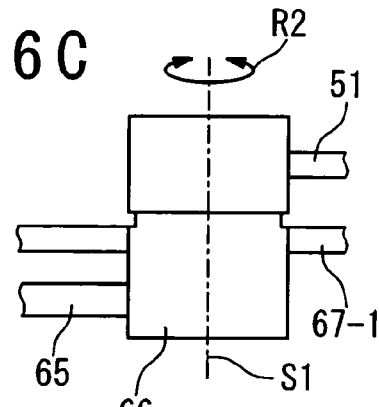
Figure 6D:
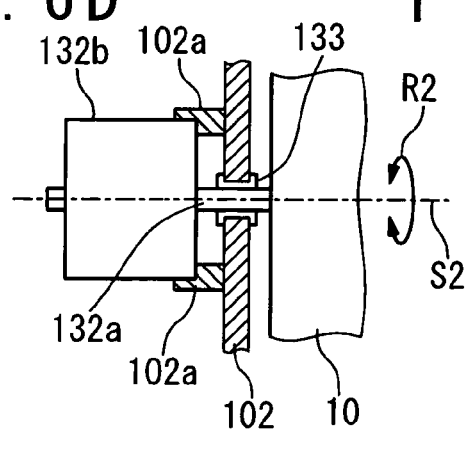
Figure 6E:
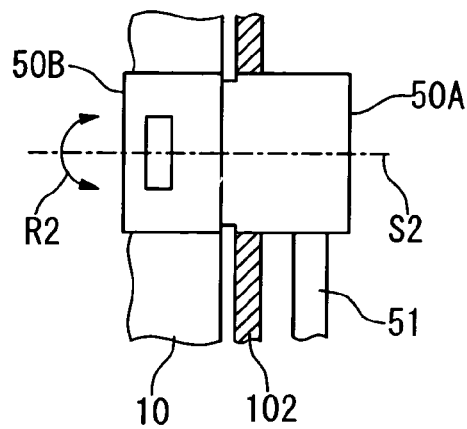

As shown in FIG. 6A, for the support frame 102, the articulation 66 (rotary RF coupler) of the waveguide tube system 61 and the S swing servo motor 131$b$ are mounted to two opposite sides, respectively, along the first swing axis S1. Similarly, a pair of rotary RF couplers 50A and 50B, and the S2 swing servo motor 132$b$ are mounted to two opposite sides which are different from the above-mentioned two sides, respectively, along the second swing axis S2. As shown in FIGS. 6A to 6C, the articulation 66 (rotary RF coupler) of the waveguide tube system 61 is mounted to the center of one of longer sides of the support frame 102, and a drive shaft 131$a$ of the S1 swing servo motor 131$b$ is mounted to the center of the opposed longer side of the frame 102 to overlap the second swing axis S1. The S1 swing servo motor 131$b$ is fixedly supported to the support frame 67-2. When the servo motor drive shaft 131$a$ is rotated, the X-ray head 10 swings around the first swing axis S1 as shown by R1 in FIG. 6B. Also, as shown in FIGS. 6A, 6D, and 6E, a pair of rotary RF couplers 50A and 50B are mounted to the center of one of the shorter sides of the support frame 102, and a drive shaft 132$a$ of the S2 swing servo motor 132$b$ is mounted to the center of the opposed shorter side of the support frame 102 to overlap the second swing axis S2. The main body section of the S2 swing servo motor 131$b$ is fixedly supported to the bracket 102$a$ on the support frame side, and the drive shaft 132$a$ is rotatably supported to the support frame 102 via a bearing 133. When the servo motor drive shaft 132$a$ is driven and rotated, the X-ray head 10 swings around the S2 drive shaft 10. As shown in FIG. 6A, the wave guide tube 51 is provided inside each of link arms 63 and 65 of the waveguide tube system 61, and a rotary RF coupler 50 is provided in each of articulations 64 and 66. The microwave is introduced into the accelerator tube 110 inside the X-ray head 10 by further passing the pair of rotary RF couplers 50A and 50B.

The rotary RF coupler provided for the articulation of waveguide to transfer microwave will be described with reference to FIGS. 7 to 9.

Figure 7:
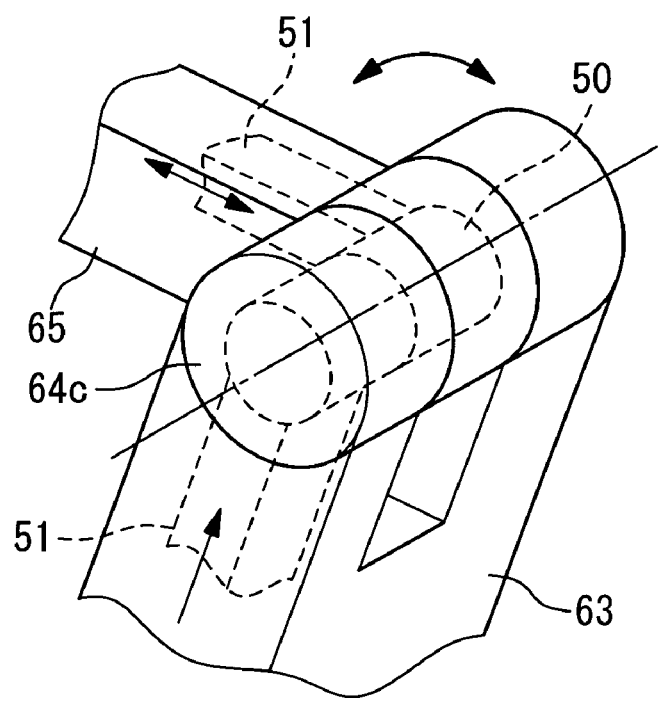
FIG. 7 is a drawing showing the configuration of an articulation section containing a rotary RF coupler.

FIG. 7 is a diagram showing the configuration of the articulation containing the rotary RF coupler 50. In FIG. 7, the articulation 64$c$ is typically shown, but the same thing applies to the articulation 64$a$, the articulation 64$b$, the articulation 66, and the pair of rotary RF couplers 50A, 50B. As shown in FIG. 7, the waveguide tube 51 is installed inside the link arms 63 and 65, and the waveguide 51 electromagnetically communicates through the rotary RF couplers 50 in the articulations 64$a$ to 64$c$, and 66.

Figure 8:
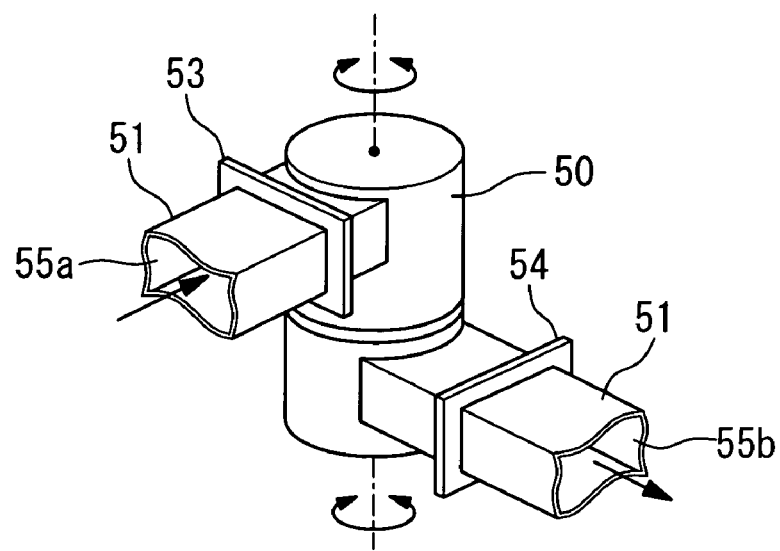
FIG. 8 is a perspective view showing the detail of the rotary RF coupler shown in FIG. 7.

FIG. 8 is a perspective view showing the detail of the configuration of the rotary RF coupler 50 shown in FIG. 7. As shown in FIG. 8, the rotary RF coupler 50 is connected to each of the waveguide tubes 51 by flange joints 53 and 54. The rotary RF coupler 50 transmits the acceleration microwave in the waveguide 55$a$ to waveguide 55$b$ through axial rotation.

Figures 9A, 9B:
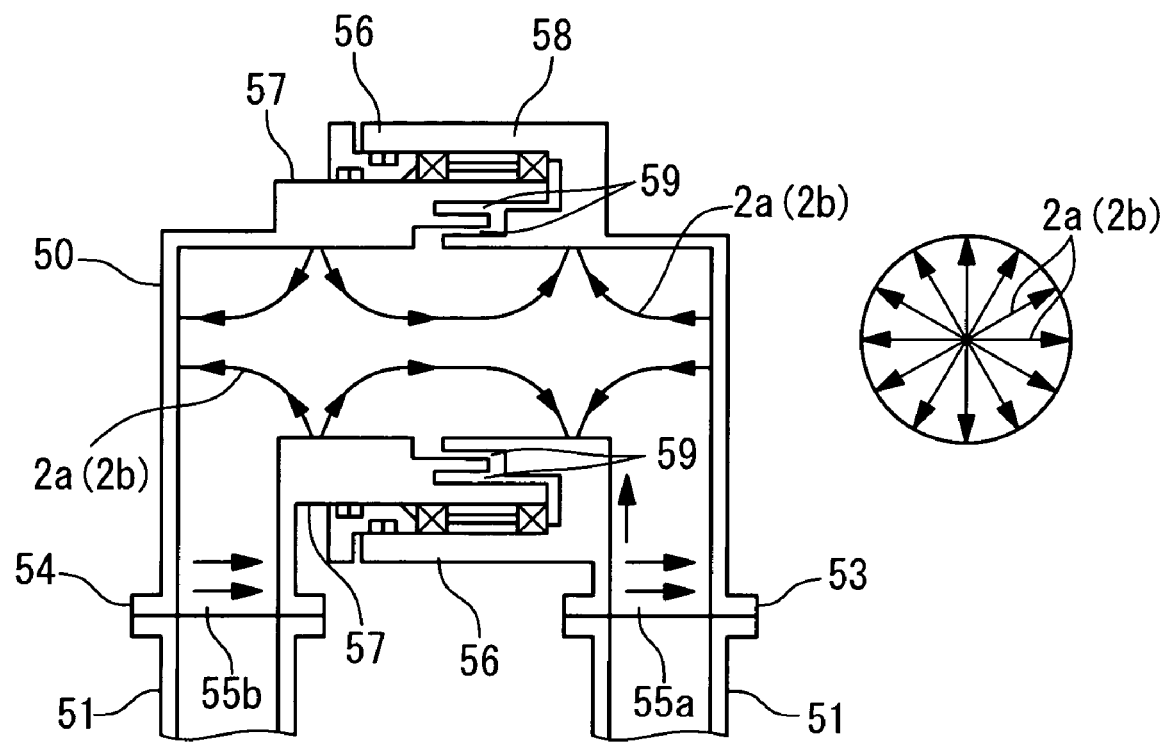
FIG. 9A is a cross sectional view showing the detail of the rotary RF coupler of FIG. 8.
FIG. 9B is a diagram showing one example of a mode of microwave in the rotary RF coupler.

FIG. 9A is a cross sectional view showing the detail of the rotary RF coupler 50 of FIG. 8. FIG. 9B shows one example of the microwave mode inside the rotary RF coupler 50. As shown in FIG. 9A, the waveguides 55$a$ and 55$b$ of the waveguide tube 51 communicate with the rotary space surrounded by rotating members 56 and 57 of the rotary RF coupler 50, a bearing 58, and $\lambda/4$ wave length choke 59, and in this, the microwave is guided by the in-tube mode (electric flux line 2$a$ (2$b$)) exemplified in FIG. 9B. By this kind of combination with the rotary RF coupler 50 and the waveguide tube 51, it is possible to smoothly supply acceleration microwaves to the traveling X-ray head 10 from the microwave generating unit 20 such as Klystron fixed to the ground.

Figure 10:
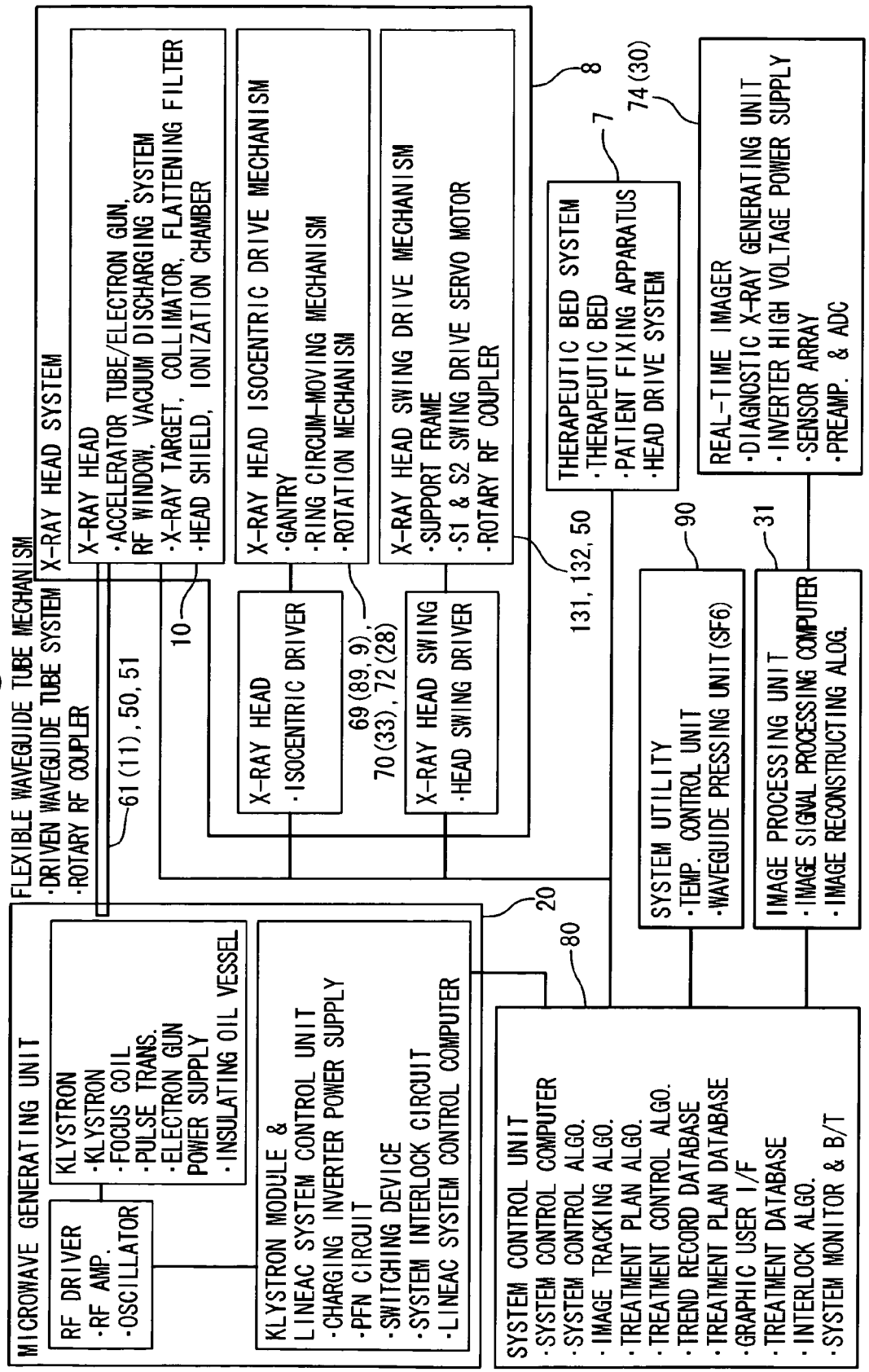
FIG. 10 is a block diagram showing a control system of the radiotherapy apparatus according to the first embodiment of the present invention.

Next, description will be made on the control system of the radiotherapy apparatus according to the present invention. FIG. 10 is a block diagram showing the control system of a radiotherapy apparatus according to the embodiment of the present invention. The control system according to this embodiment includes the therapeutic bed system 7, an X-ray head system 8, the real-time imager 74, an image processing unit 31, the microwave generating unit 20, the system control unit 80, and a system utility 90. Practically, a system configuration in which the system control unit 80 administers and controls the whole is adopted.

The system control unit 80 is provided with a system control computer, and includes a system control algorithm, image tracking algorithm, radiotherapy plan algorithm, radiotherapy control algorithm, graphical user interface (GUI) and interlock algorithm as computer programs, and a radiotherapy plan database, a trend record database, and a radiotherapy database are provided. In addition, the system controller includes a system monitor (display unit) I/O units, and BIT, and with these at the center, other system blocks are connected, respectively, and I/O signals are exchanged.

The radiotherapy plan database stores the radiotherapy plan data as the data concerning the radiotherapy plan which a doctor designs. The radiotherapy plan data is based on various inspections carried out before an operation. The radiotherapy plan data correlates the patient attribute data, patient image data, absorbed dose data, the therapeutic dose data, and diseased part position data with each other. However, the patient attribute data indicates data of the patient 4 such as name and birthday. The patient image data indicates the X-ray tomography pictures of the patient 4. The absorbed dose data relates to the absorbed dose of radiation (X-rays) to the diseased part 5 and the irradiation method (frequency, absorbed dose for one time, irradiation direction (route)). The therapeutic dose data relates to the therapeutic dose setting that indicates the radiation for the diseased part 5 (X-ray), the irradiation method (frequency, absorbed dose for one time, irradiation direction (route)). The diseased part position data relates to the position of the diseased part 5. The position of the affected-portion 5 may be in the defined region 5-1 to be described later.

The trend record database stores irradiation resultant data concerning the actual performance of radiotherapy. The irradiation resultant data relates to radiation (X-rays) actually irradiated at the time of radiotherapy. The irradiation resultant data correlates the patient attribute data, integrated therapeutic dose, integrated dosage, the therapeutic dose for each irradiation direction (portal number), estimated dosage, target coordinates (coordinates of irradiation target in diseased part 5), and machine coordinates (coordinates of radiation field 5' actually irradiated) with each other. The radiotherapy database stores the kind of substances and radiation dosage curve to indicate the relationship between the thickness of substances and radiation (X-ray) dosage, and others by correlating them with each other.

The system control algorithm controls the whole system control unit 80 such as each algorithm, GUI, system monitor (display unit), I/O units, and BIT. The radiotherapy plan algorithm calculates the therapeutic dose data (the therapeutic dose of X-rays per each irradiation direction (route) and integrated therapeutic dose), based on the radiotherapy database (X-ray tomography images of the patient 4, dosage data) and the radiotherapy database (radiation dosage curve for each substance). The results are displayed on the display unit and are verified by the doctor or physician. The doctor or physician varies the irradiation directions and X-ray dosage to obtain the desired the therapeutic dose data. After the verification, the results are stored in the radiotherapy plan database.

The radiotherapy control algorithm controls an X-ray head system 8 so that the X-ray head 10 is directed to the specified direction in accordance with the radiotherapy plan data of the radiotherapy plan database and/or X-ray head 10 swing rate from the image tracking algorithm. Also, the radiotherapy control algorithm stores the irradiation resultant data obtained from image processing unit 31, the X-ray head system 8, and the image tracking algorithm during the radiotherapy in the trend record database.

The image tracking algorithm calculates the coordinates of the diseased part 5 in accordance with the tracking image data obtained from the image processing unit 31. Also, based on various data obtained from the X-ray head system 8, the coordinates of the radiation field 5' of the X-ray head 10 are found. Based on the coordinates of the diseased part 5 and coordinates of radiation field 5', swing of the X-ray head 10 is calculated.

The interlock algorithm allows the therapeutic X-ray 3*a* and the diagnostic X-ray 3*b* to make an emergency stop when specified conditions are satisfied. The specified conditions include a case that the emergency stop button is pressed, a case that the radiation field 5' and the diseased part 5 are separated by more than the preset distance, and at least one of a case in which the therapeutic dose and dosage to the patient 4 exceeds the relevant present allowable value, a case in which the therapeutic X-ray 3*a* is stopped to irradiate the diagnostic X-ray 3*b*, and a case in which the diagnostic X-ray 3*b* is stopped to irradiate the therapeutic X-ray 3*a*.

The X-ray transmission data detected by the real-time imager 74 is reconstructed to a diagnostic image by the image restructuring algorithm in the image processing unit 31, and transmitted to the system control unit 80. By this, the diagnosis image is formed in real time during the radiotherapy, and the doctor or physician is able to carry out the radiotherapy while watching the diagnostic images displayed on the compute display unit of the system control unit 80.

The microwave generating unit 20 includes a Klystron modulator and lineac system controller, Klystron, and RF driver. Klystron is connected to the X-ray head 10 via the waveguide tube system 61, and is the supply source to supply the microwave to the accelerator tube 110.

The X-ray head system 8 includes the X-ray head 10, isocentric drive mechanism (including the O-type gantry 69, the ring circumferential moving mechanism 70, and the gantry rotating mechanism 72), and a swing drive mechanism (including the first swing mechanism 131, the second swing mechanism 132, and the rotary RF coupler 50). The isocentric drive mechanism and the swing drive mechanism are connected to the system control unit 80 via each driver (isocentric driver and swing driver), and the isocentric drive mechanism of the X-ray head 10 during the isocentric irradiation and 2-axis swing drive mechanism of the X-ray head 10 at the time of pseudo-isocentric irradiation are controlled.

Next, the operation of the radiotherapy apparatus according to the first embodiment of the present invention will be described.

First of all, the position is calibrated. The position is calibrated by the use of a CCD camera 60 installed to allow the center of the light receiving surface to overlap the isocenter 5*a* and to keep the light receiving surface horizontal, and a laser transmitter installed in the X-ray head 10 to imitate the electron lineac. The deviation between the laser light receiving point and the isocenter 5*a* is designated as a compensation value.

Through the above-mentioned position calibration method, the positional deviation by strain at the time of fabrication, deflection by dead weight, displacement by stress at the time of installation can be corrected highly accurately in large machined workpieces such as the O-type gantry 69 in a short time, and the positional accuracy can be improved. In the present embodiment, it becomes possible to achieve about 20-µm positional resolution. This kind of position calibration is carried out when the radiotherapy apparatus 6 is installed and during periodical inspection. However, the position may be calibrated for each designated use frequency and each radiotherapy.

Figure 11:
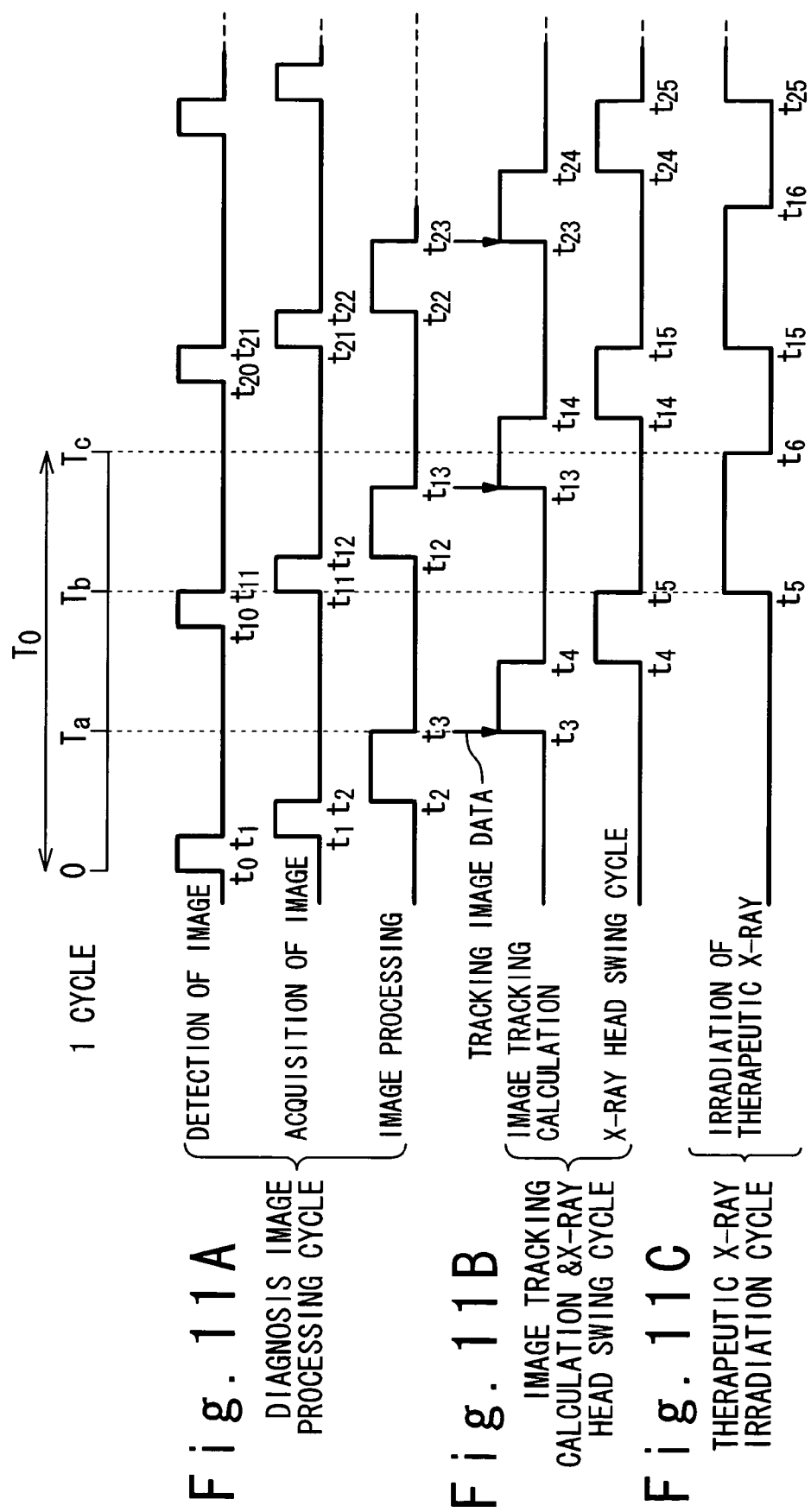
FIGS. 11A to 11C are timing charts in the operation of the radiotherapy apparatus according to the first embodiment of the present invention.

Now, the operation of the radiotherapy apparatus according to the embodiment of the present invention will be described. FIGS. 11A to 11C are timing charts in the operation of the radiotherapy apparatus according to the first embodiment of the present invention. FIG. 11A shows the timing of the operation to process diagnostic images, FIG. 11B the timing of image tracking calculation based on the diagnostic image after processing and swing operation of the X-ray head 10, and FIG. 11C the timing of irradiation of the therapeutic X-rays, respectively.

(0) Before Time t0:

First of all, the main switch of the radiotherapy apparatus 6 is turned ON and the power supplies of the therapeutic bed system 7, the X-ray head system 8, the real-time imager 74, the microwave generating unit 20, the system control unit 80, and the system utility 90 are set to the wait state. The therapeutic bed system 7 operates to move the patient 4 into the therapeutic area together with the therapeutic bed 7-2, and the real-time imager 74 operates to move the therapeutic bed 7-2, and brings the diseased part 5 into line with the isocenter 5a of therapy apparatus for position adjustment. Upon completion of this isocentric positioning, the real-time image diagnosis by the real-time imager 74 and radiotherapy by using the X-ray head 10 begin.

(1) Step S2-1: Period from Time t0 to Time t1

In general, the diagnostic X-ray 3b is irradiated to the radiation field 5' from the diagnostic X-ray generation unit. By the sensor array of the X-ray camera (real-time imager 74), the X-ray transmission data is detected as the diagnostic image data. In order to minimize exposure, the irradiation time of diagnostic X-ray 3b is limited to a period from time t0 to time t1.

(2) Step S2-2: Time t1 to t2

The detected diagnostic image data is converted to current signals proportional to transmission X-ray dose, and is taken into an image signal digitizer and a data recording apparatus via a main AMP.

(3) Step S2-3: Period From Time t2 to Time t3

The recorded diagnostic image data is outputted from the data recorder to the image processing unit 31. The data is arithmetically processed by the use of the image reconstruct algorithm of the image processing unit 31, and converted to the tracking image data. The tracking image data indicates the diagnostic images at each coordinate point (Xi, Yi, Zi) (i=1–n: n is the number of data) of the coordinate system of the radiotherapy apparatus 6A. The tracking image data is outputted to the system control unit 80. The tracking image data is reproduced and displayed on the display unit of the system control unit 80 as the diagnostic images of the diseased part 5.

The real-time imager 74 and the image processing unit 31 repeat the process in a period from time t0 to time t3 again after the specified time elapses after time t3. In FIGS. 11A to 11C, the process of time t0 to t3 is same as the process in a period from time t10 to time t13, and the process in a period from time t20 to time t23. In order to prevent the direct X-ray, leak X-ray, and scattered X-ray of the therapeutic X-ray 3a from affecting the sensor array (detector) of the real-time imager 74, the X-ray head 10 is interlocked to prevent the therapeutic X-ray 3a from being irradiated at least during time t0 to t1 during which the diagnostic X-ray 3b is being irradiated. The total period from time t0 to time t3 for processing these diagnostic images (Step S2-1 to S2-3) is 0.01 second. That is, one cycle time for the diagnostic image processing is 0.01 second. This is a sufficient sample rate for tracking quick motions such as heart pulses.

(4) Step S2-4: Time t3 to t4

Using the image tracking algorithm of the system control unit 80, the following image tracking calculation is carried out.

The coordinates of the diseased part 5 (coordinate point (X, Y, Z) in the coordinate system of the radiotherapy apparatus 6) is extracted based on the tracking image data. On the other hand, the current position (coordinate point in the coordinate system of the radiotherapy apparatus 6 (x, y, z)) of the radiation field 5' of the X-ray head 10 is calculated based on the ring circumferential moving mechanism 70, gantry rotating mechanism 73, position (coordinates) of the first swing mechanism 131 and the second swing mechanism 132, a rotating angle. Based on the calculated coordinates, [1] when the distance L (=|(X, Y, Z)−(x, y, z)|) between two points is equal to or less than a preset value $L_{02}$, the swing operation is not carried out, and [2] when the distance L is greater than the preset value $L_{01}$, the swing angle is set to $\theta_0$ (which corresponds to the distance $L_{01}$ in the coordinate direction of the diseased part 5), and [3] when $L_{02}$<distance L<$L_{01}$, the swing angle ($\theta 1$, $\theta 2$) of the X-ray head 10 is calculated based on the coordinates of the diseased part 5 as well as the coordinates of the radiation field 5'. Here, the swing angle ($\theta 1$, $\theta 2$) of the X-ray head 10 means $\theta 1$ (rotating direction and size of rotating angle) of small displacement angle (swing angle) around the S1 swing drive axis and $\theta_2$ (turn direction and magnitude of angle) of small displacement angle (swing angle) around the S2 swing drive axis. $L_{01}$ means the maximum distance that the X-ray head 10 can swing between time t4 and t5, and $L_{02}$ is an error estimated when the coordinate point (X, Y, Z) of the diseased part 5 and the coordinate point (x, y, z) of the radiation field 5' are calculated.

The state of motion of this diseased part 5 (coordinate point (X, Y, Z)) is displayed on the display unit of the system control unit 80. In this case, not only the diseased part 5 but also the surrounding region (example: frame 5-2 including the diseased part 5 (to be described later)) may be displayed in the same manner.

(5) Step S2-5: Time t4 to t5

A swing drive signal is outputted to the X-ray head system 8 based on the calculated swing angle ($\theta 1$, $\theta 2$) of the X-ray head 10 by the radiotherapy control algorithm of the system control unit 80 to indicate the swing angle ($\theta 1$, $\theta 2$) of the X-ray head 10. The first swing mechanism 131 and the second swing mechanism 132 are driven by the X-ray head swing driver of the X-ray head system 8, in response to the swing drive signal, so that the X-ray head 10 is directed to a desired direction.

The system control unit 80 repeats the process from time t3 to time t5 from time t13 after time t5. In FIGS. 11A to 11C, the process from time t3 to time t5 is same as the process from time t13 to time t15, and the process from time t23 to time t25. The total time period from t3 to t5 for these image tracking calculation and the X-ray head swing (Step S2-4 to S2-5) is 0.01 second. That is, one cycle time for the image tracking calculation and the X-ray head swing is 0.01 second. This is a sufficient sample rate for tracking quick motions such as heart pulses.

There is a possibility of an erroneous swing operation during the time period from time t4 to time t5 during which the S1 swing servo motor 131b of the first swing mechanism 131 and the S2 swing servo motor 132b of the second swing mechanism 132 are driven. Therefore, the X-ray head 10 is interlocked during such a period to prevent the therapeutic X-ray 3a from being irradiated. Thus, safety is secured.

(6) Step S2-6: Time t5 to t6

Using the system control algorithm of the system control unit 80, at time t5, the therapeutic X-ray irradiation signal is outputted to the X-ray head 10 to instruct irradiation of the therapeutic X-ray 3a. The X-ray head 10 is released from the interlocked state, and irradiation of the therapeutic X-ray 3a to the diseased part 5 begins. The irradiation period from time t5 to time t6 of the therapeutic X-ray 3 is about 0.0025 to 0.01 second. The irradiation duty is about 50%.

The system control unit 80 repeats the process from time t5 to time t6 from time t15 after time t6. In FIGS. 11A to 11C, the process from time t5 to time t6 is same as a process from time t15 to time t16, and a process from time t25 to time t26.

The total period from time t5 to time t6 for irradiation of the therapeutic X-rays (Step S2-6) is 0.01 second. That is, one cycle time for irradiation of the therapeutic X-rays is 0.01 second. This is a sufficient sample rate for tracking quick motions such as heart pulses.

Referring now to the drawings, how to irradiate the therapeutic X-ray 3a to the subject while the X-ray head 10 is being swung will be described.

Figure 12:
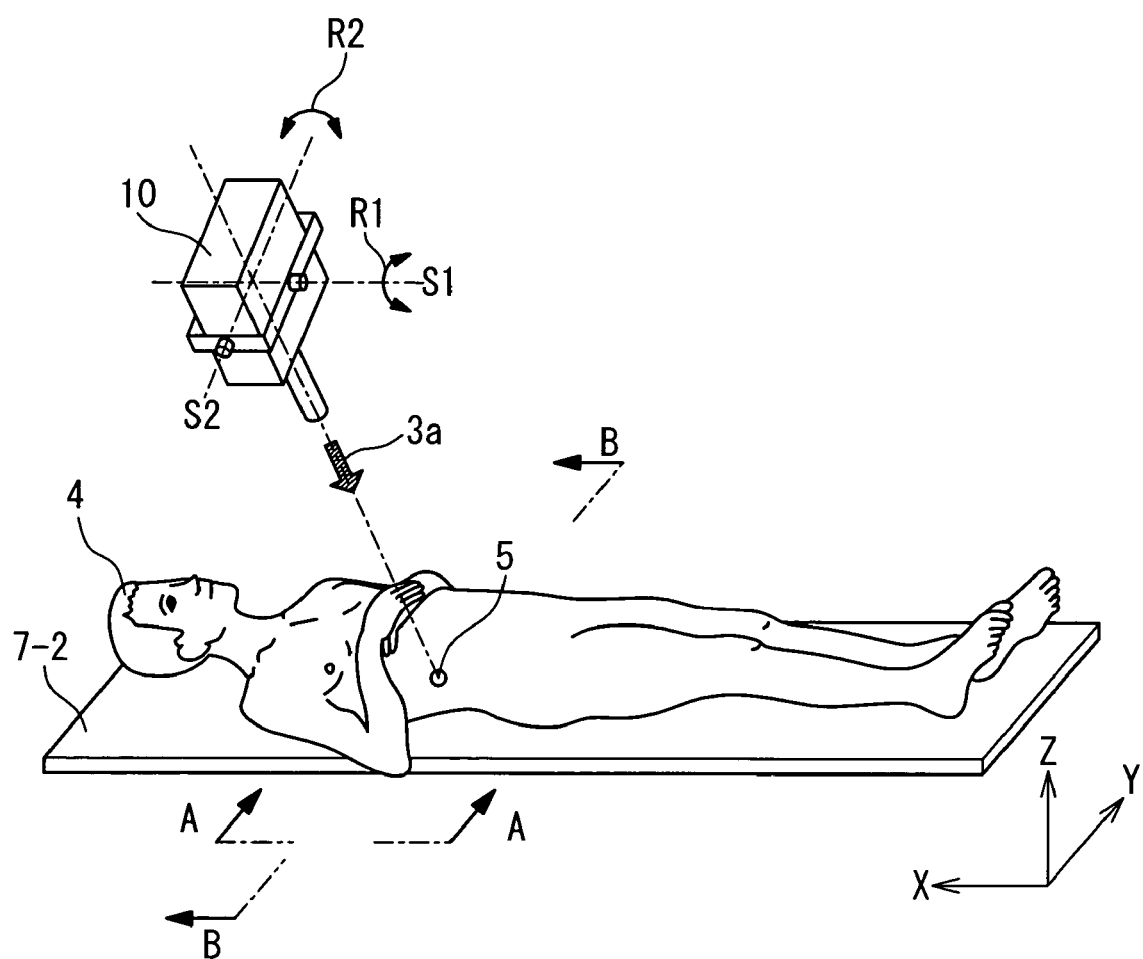
FIG. 12 is a perspective view showing the manner of radiotherapy using an X-ray head.
Figure 13:
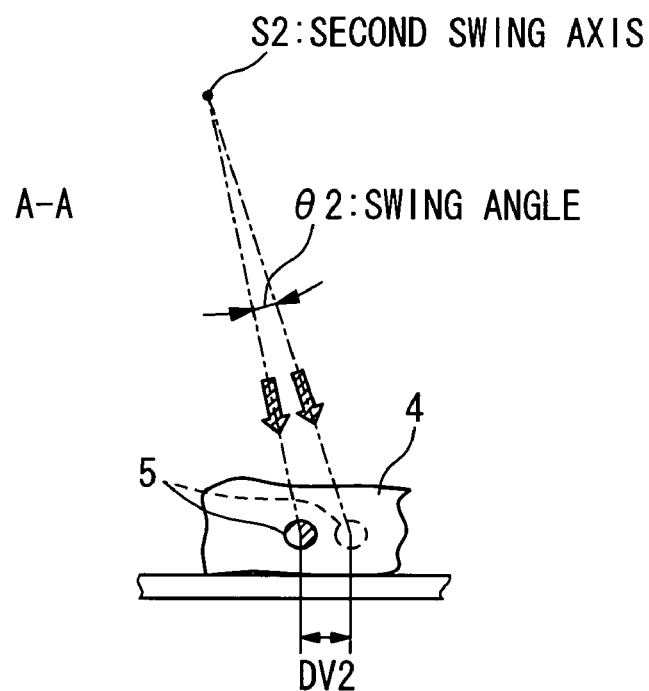
FIG. 13 is a cross sectional view of a patient along line A—A in FIG. 12.
Figure 14:
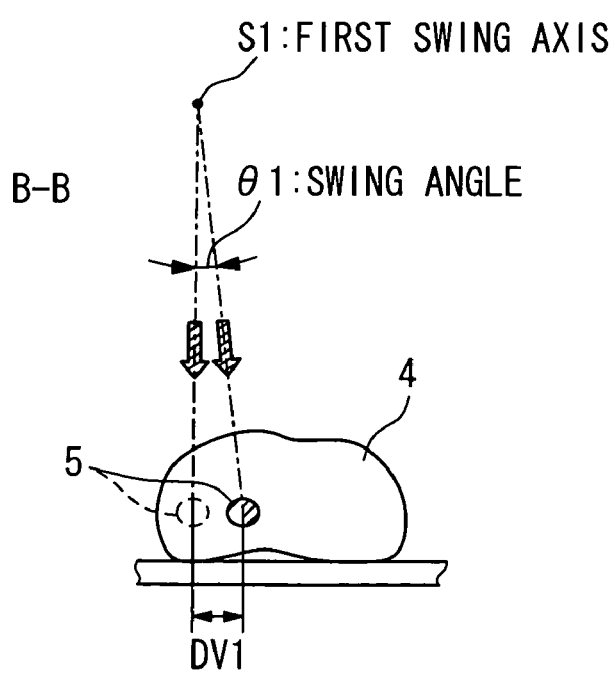
FIG. 14 is a cross sectional view of the patient along line B—B in FIG. 12.

FIG. 12 is a perspective view showing the manner of radiotherapy by the X-ray head 10. The X-ray head 10 irradiates the X-ray head 10 to the diseased part 5. FIG. 13 is a cross sectional view of the patient along the line A—A in FIG. 12, while FIG. 14 is a cross sectional view of the patient along the line B—B in FIG. 12. FIG. 13 and FIG. 14 are diagrams showing the manner how the therapeutic X-ray 3a is struck while the X-ray head 10 is being swung.

In order to irradiate the X-rays while tracking the movement of the radiation field 5', in the period from time t3 to t4, the system control unit 80 calculates shift quantities DV1 and DV2 of the diseased part 5 from the radiation field 5' in the X-axis direction and Y-axis direction based on the calculated position of the diseased part 5 (coordinate (X, Y, Z)) and the present coordinate (x, y, z) of the radiation field 5' of the X-ray head 10. Then, displacement angles θ1 and θ2 through the movement around the first swing drive axis S1 and the second swing drive axis S2 are calculated based on the shift quantities DV1 and DV2, using a specified calculation equation.

In the above-mentioned time period from time t5 to time t6, the X-ray head 10 is swung around the first swing drive axis S1 by displacement angle θ1 and around the second swing drive axis S2 by displacement angle θ2. Then, as soon as the swing operation is stopped, the therapeutic X-ray 3a is emitted from the X-ray head 10.

Through the above steps S2-1 to S2-6, sights of the X-ray head 10 tracks the diseased part 5 quickly and at a high precision response even if the diseased part 5 is below the neck, and such as a tumor under the influence of movements and state of organs such as breathing, heart pulses, vermiculation, and urine volume in a bladder. Thus, it is possible to irradiate radiation (X-ray) to the diseased part at high accuracy. That is, within 0.03 second including the processing time of the diagnostic images, the X-ray head 10 can be swung and irradiate radiation (X-ray) to the diseased part. Thus, the X-ray head 10 can quickly follow the movement of the radiation field (diseased part).

In the above process, the angle of the swing operation of the X-ray head 10 in the step S2-5 is limited to a predetermined range during the period from time t3 to time t4 in the step S2-4. This is because as the swing angle increases, the time for the swing operation increases, so that the diseased part 5 moves further. As a result, the coordinate point (x, y, z) of the radiation field 5' of the X-ray head 10 would greatly deviate from the position of the coordinate point (X, Y, Z) of the diseased part 5.

The quick movement of the diseased part 5 followed by the X-ray head 10 is mainly through breathing and heart pulses. In such a case, the diseased part 5 generally moves in the same region (however, the route is not always same).

Consequently, even if the coordinate point (x, y, z) of the radiation field 5' of the X-ray head 10 does not completely coincide with the coordinate point (X, Y, Z) of the diseased part 5, it is possible to bring them in line thereafter.

When any trouble occurs in the acquisition of the diagnostic image data or image tracking calculation, the therapeutic X-ray 3a is interlocked to stop irradiation at that point of time, and safety is secured. The therapy apparatus of the present invention is designed to carry out irradiation of the therapeutic X-ray 3a after it is confirmed that the swing operation and the positioning operation of the X-ray head 10 are properly carried out.

When the deviation of the coordinate point (x, y, z) of the radiation field 5' from the coordinate point (X, Y, Z) of the diseased part 5 is greater than a preset value, irradiation of the therapeutic X-ray 3a in Step S2-6 (time t5 to t6) is not carried out.

Also, the system control unit 80 can move the ring circumferential moving mechanism 70, the gantry rotating mechanism 72, and the therapeutic bed system 7 as required, such that the sight of the X-ray head 10 can be aligned to the diseased part 5. That is, the system control unit 80 calculates the swing quantities (for first swing mechanism 131 and the second swing mechanism 132) and the movement quantity (for the ring circumferential moving mechanism 70, gantry rotating mechanism 73, and the therapeutic bed system 7) of the X-ray head 10 in the period from time t3 to time t4 based on the coordinate of the diseased part 5 and the coordinate of the radiation field 5'. Next, in the period from time t4 to time t5, the swing quantities and the movement quantity of the X-ray head 10 are outputted to the X-ray head system 8. Then, the first swing mechanism 131, the second swing mechanism 132, the ring circumferential moving mechanism 70, the gantry rotating mechanism 73, and the therapeutic bed system 7 are moved to align the sight of the X-ray head 10 to the diseased part 5.

After the irradiation of the therapeutic X-ray 3a is stopped, the irradiation of diagnostic X-ray 3b begins at timing t5, and the process advances to the next diagnostic image processing cycle from time t5 to time t8. Then, at timing t3 after the diagnostic image processing, interlock of the X-ray head 10 is cancelled and the irradiation of the therapeutic X-ray 3a is restarted.

In this way, the cycle of a total of 0.03 second, namely, 0.01 second for the diagnostic image processing cycle (0-Ta in FIG. 11A), 0.01 second for the image tracking calculation cycle and X-ray head swing cycle (Ta to Tb in FIG. 11B), and 0.01 second for the therapeutic X-ray irradiation cycle (Tb to Tc in FIG. 11C) is repeated. That is, in a cycle shorter than 1/30 second (=0.033 second), the radiation head can be accurately directed to the irradiation subject. Thus, even if the diseased part (radiation field) has the quickest movement such as heart pulse, the irradiation subject can be accurately tracked in real time and radiation can be struck.

Next the procedure of pseudo non-isocentric therapy will be described below. FIGS. 15A to 15F are diagrams showing a flow of the procedure of pseudo non-isocentric therapy on the display unit.

(1) Step S3-1

In radiotherapy, a doctor or physician creates a radiotherapy plan. The radiotherapy plan is based on various examinations carried out before an operation. These radiotherapy plans are stored in the radiotherapy plan database. Also, the doctor or physician can carry out radiotherapy with high accuracy and high reliability by image-diagnosing the seat of disease at the diseased part directly in real time by the use of the radiotherapy apparatus of the present invention during the operation.

(2) Step S3-2

Figure 15A:
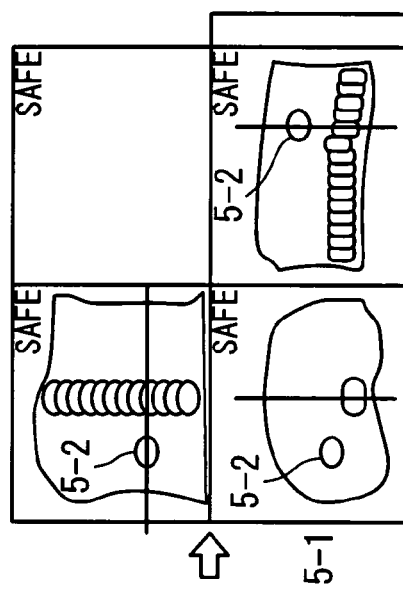
FIGS. 15A to 15F are diagrams showing a flow of the procedure of pseudo non-isocentric therapy on a display unit.

As shown in FIG. 15A, the diagnostic images of the diseased part 5 and the vicinity area are reconstructed, reproduced and displayed on the display unit of the system control unit 80 using the real-time imager 74 and the image processing unit 31. The diagnostic images are reconstructed by the above-mentioned step S2-1 to S2-3. However, on this stage, the steps S2-4 to S2-6 are not carried out.

(3) Step S3-3

Figure 15B:
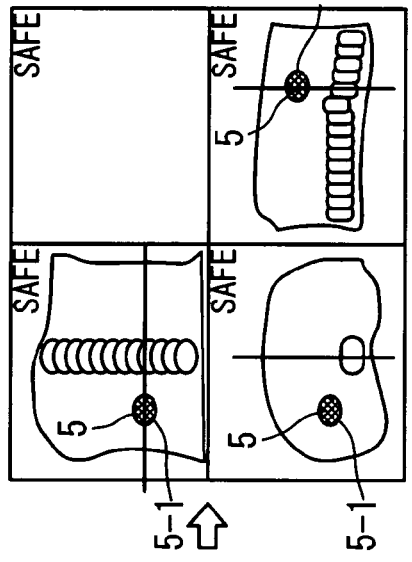

As shown in FIG. 15B, the doctor or physician confirms each tomography figure of the diseased part on a display unit, and defines the frame of the radiation field 5' for image tracking. Here, before starting therapy, mapping of the radiation field 5' is completed (radiotherapy plan database). Therefore, the radiotherapy plan database is referred to, to define the frame of the radiation field 5' in multiple slices. The region defined by the frame is a definition region 5-1. The definition region 5-1 includes the diseased part 5, and the definition region 5-1 is stored in the radiotherapy plan database.

The radiotherapy plan algorithm calculates the therapeutic dose data (X-ray for each irradiation direction (route) and integral therapeutic dose) on the basis of the radiotherapy plan database (including the definition region 5-1) and the radiotherapy database. The calculation results are displayed on the display unit and are verified by the doctor or physician. The doctor or physician varies the irradiating direction and x-ray dosage, as necessary, to obtain desired therapeutic dose data. After verification by the doctor or physician, the therapeutic dose data is stored in the radiotherapy plan database.

(4) Step S3-4

Figure 15C:
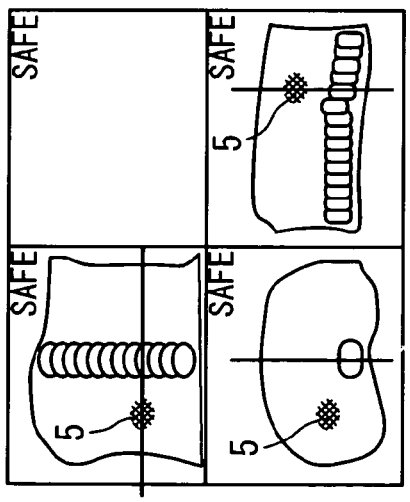

As shown in FIG. 15C, by the image tracking algorithm of the system control unit 80, the image frame extraction is carried out. That is, pattern-matching is carried out between the frame of the definition region 5-1 and the diagnostic image of the actual diseased part 5, and a frame is displayed as the frame 5-2 (to be described later). Then, the image tracking operation is started, and the doctor or physician visually checks the image tracking status.

The image tracking operation is carried out in the above-mentioned step S2-4. Consequently, the steps S2-1 to S2-4 are repeatedly carried out. However, in this stage, the steps S2-5 to S2-6 are not carried out.

(5) Step S3-5

Figure 15D:
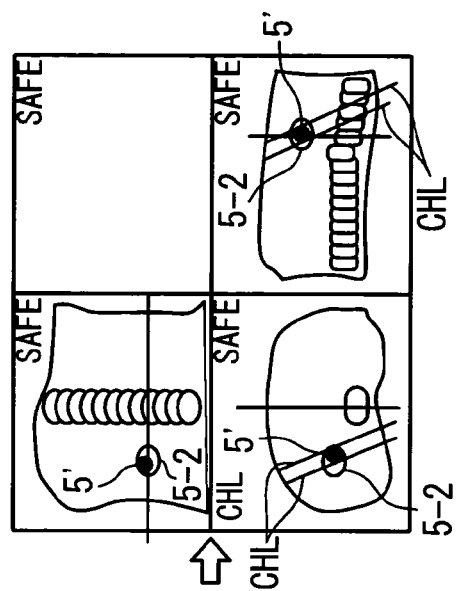

As shown in FIG. 15D, after the image tracking operation becomes stable, the doctor or physician operates a master arm switch (Master Arm SW) to set the X-ray head system 8 to an ARMED state. The X-ray head system 8 displays an irradiation volume in red with the sight indicated by crosshairs on the display unit. At the same time as the image tracking operation, the tracking operation or swinging operation of the X-ray head 10 is carried out. Thus, the sight of the X-ray head 10 and irradiation volume automatically follow as the radiation field 5' moves.

The tracking operation or swinging operation of the X-ray head 10 is carried out at the step S2-5. Consequently, the above-mentioned steps S2-1 to S2-5 are repeatedly carried out. However, in this stage, the therapeutic X-ray 3a is not irradiated, and the step S2-6 is not carried out.

(6) Step S3-6

Figure 15E:
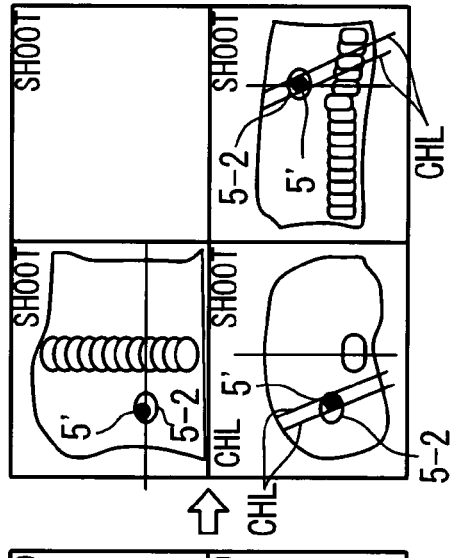

As shown in FIG. 15E, irradiation of the therapeutic X-ray 3a is started based on a trigger operation of the doctor or physician. In the stage of radiotherapy plan, the planned irradiation time is determined, and countdown is started on the display unit. On the other hand, the irradiation time of one irradiation shot (Step S2-6: time t5 to t6) is determined. Thus, while the short-time irradiation (time t5 to t6) is repeated, the count is decreased. When the count finally reaches zero, the therapeutic X-ray 3a automatically stops. The therapeutic dose of the therapeutic X-ray 3a is detected by the ionization chamber 126 and is outputted to the radiotherapy control algorithm. The irradiation of therapeutic X-ray 3a is carried out at the step S2-6. Consequently, the above-mentioned steps S2-1 to 2-6 are repeatedly carried out.

In addition, by the radiotherapy control algorithm, (whole or part of) the irradiation resultant data obtained during the radiotherapy from the image processing unit 31, the X-ray head system 8, and the image tracking algorithm is continuously displayed on the display unit. While the doctor or physician confirms (whole or part of) this irradiation resultant data, the doctor or physician continues to pull the trigger to continue the irradiation. The irradiation resultant data is stored in the trend record database.

The system control unit 80 carries out the sampling (tracking) of the diagnostic images and irradiation of the therapeutic X-ray 3a alternately and repeatedly at high speed in real time. The irradiation of the therapeutic X-ray 3a immediately stops at the timing when the doctor or physician releases the trigger, even before the count reaches zero, and in this way, safety is sufficiently secured.

(7) Step S3-7

Figure 15F:
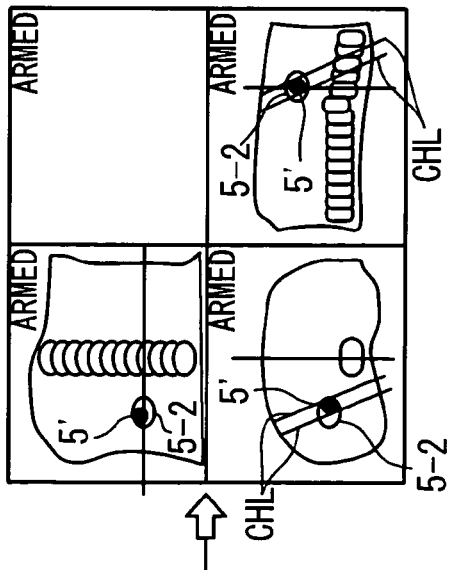

As shown in FIG. 15F, the doctor or physician sets the Master Arm SW to a SAFE position to bring the system in a safe condition, and moves the X-ray head 10 to the next irradiating position. In this stage, the operation at the steps S2-1 to S2-3 is carried out, and the operation at the steps S2-4 to S2-6 is not carried out.

The doctor or physician confirms a total dose as an accumulated dose at the end of irradiation in each portal and at the end of a series of irradiations. That is, by the radiotherapy control algorithm, the doctor or physician reads the data from the trend record database, and displays the accumulated dose and the accumulated dose distribution in one cycle on the display unit. The data concerning radiotherapy is stored in the radiotherapy file (including the irradiation resultant data) provided for each patient 4 in the trend record database.

Now, the method to pattern-matching the diagnostic image of the actual diseased part 5 with the frame of the definition region 5-1 at the step S3-4 will be further described.

Figure 16C:
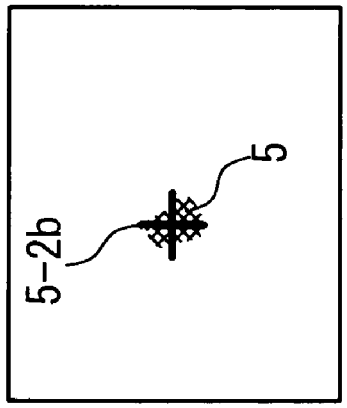
FIGS. 16A to 16E are diagrams showing a relationship between the diseased part and a definition region and a frame by pattern matching.
Figure 16D:
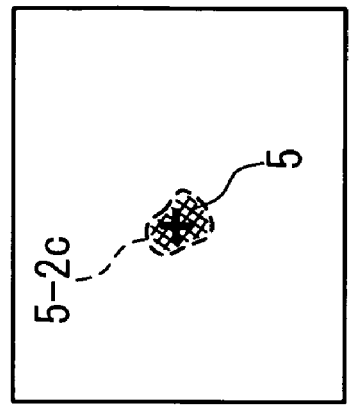
Figure 16B:
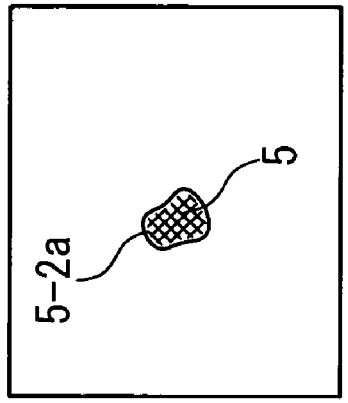
Figure 16E:
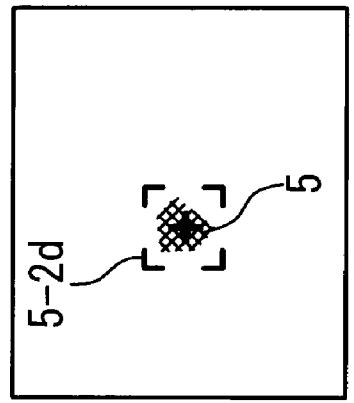
Figure 16A:
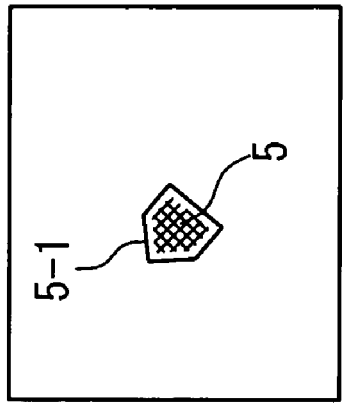

FIGS. 16A to 16E are diagrams showing a relationship between the diseased part 5 and the definition region 5-1 and the frame 5-2 by pattern matching. FIG. 16A indicates a relationship between the diseased part 5 and the definition region 5-1, and FIGS. 16B to 16E show a relationship between the diseased part 5 and the frame 5-2.

(1) Step S4-1

The doctor or physician shows the definition region 5-1 on the display unit by a touch pen or a pointing device like a mouse on the display unit.

(2) Step S4-2

The radiotherapy plan algorithm extracts the diagnostic image in the definition region 5-1 based on the definition region 5-1 drawn on the display unit and the diagnostic image on the display unit. Thus, the radiotherapy plan algorithm grasps the shape, coordinate, and brightness distribution of the diagnostic image. Or, the radiotherapy plan algorithm grasps the shape, coordinate, and brightness distribution of the diagnostic image by extracting the shape of the brightness range for a predetermined ratio (for example, 90%) of the definition region 5-1 shown in FIG. 16B.

(3) Step S4-3

The radiotherapy plan algorithm calculates the center of gravity for the shape of the range of the definition region 5-1 or the shape of the brightness range which indicates the predetermined ratio. The algorithm displays the calculation result by "+" on the display unit. For example, the center of gravity of the definition region 5-1 (FIG. 16A) is shown in FIG. 16C. The center of gravity of the brightness range (FIG. 16B) for the predetermined ratio is shown in FIG. 16D. By the way, as shown in FIG. 16E, only the center of the definition region 5-1 may be simply shown.

Through the above, the pattern matching is ended.

Figure 17:
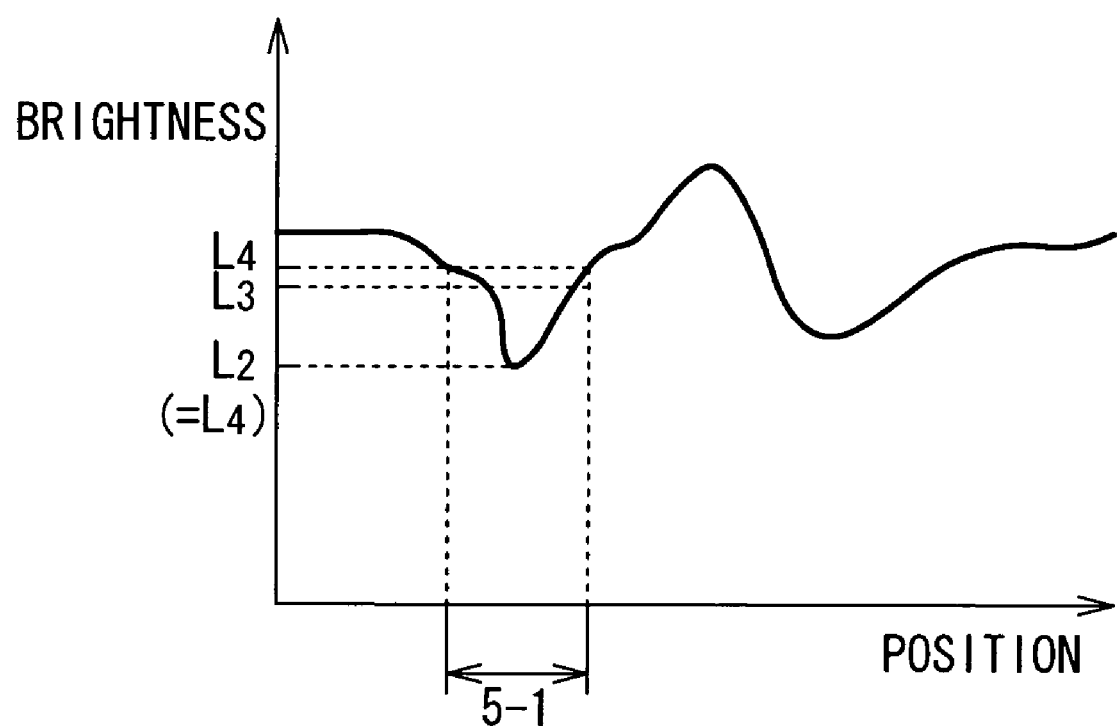
FIG. 17 is a graph showing one example of a brightness distribution in a diagnostic image.

Also, it is possible to carry out binary display in which the range of the definition region 5-1 or the brightness range for the predetermined ratio is displayed in a specific color and others in another color on the display unit. In this case, grasping of the brightness distribution is carried out as follows. FIG. 17 is a graph showing one example of brightness distribution in the diagnostic image. The data is plotted in which the vertical axis shows brightness and the horizontal axis shows the position of the diagnostic image. The graph indicates that the brightness in the definition region 5-1 of the diagnostic image is in the range of L1 to L2. Consequently, the brightness range of the definition region 5-1 is L1 to L2. Also, the brightness range for the predetermined ratio of the definition region 5-1 (example: 90%) is a continuous brightness range L3 to L4 which is selected in such a manner as to occupy the area of the predetermined ratio (example: 90%) in the definition region 5-1 of the brightness range L1 to L2. In such a case, L2=L4. It should be noted that since other positions that indicate the same brightness are apart from the definition region 5-1, they are not recognized.

According to the therapy apparatus of the present embodiment, the radiation irradiating head (X-ray head 10) can be swung within 0.02 seconds including the diagnostic image processing to follow the movement of the radiation field (diseased part). Therefore, it is possible to irradiate the therapeutic X-ray to the radiation field at a high accuracy (radiation time: 0.01 second). In this way, it is possible to carry out non-isocentric irradiation at high-speed response and in high accuracy based on the movement of the diseased part. Therefore, it is possible to accept as radiotherapy subjects diseased parts below the neck, e.g., tumors under the influence of movements and conditions of the organs, such as breathing, heart pulses, vermiculation, and urine volume in a bladder.

It is not possible to use the imaging for the soft tissues with low contrast. Therefore, the positioning of the radiation field should be carried out by using an X-ray CT, and MRI, based on landmarks with high contrast such as bone tissue. Or, small-size gold plates are embedded in the vicinity of the radiation field to use them as markers, or image enhancement is carried out by using contrast agents or through differential image processing as in a case of DSA (Digital Subtraction Angiography). Also, in the X-ray CT and PET, high-speed real-time image reconstruction calculation is carried out for real-time imaging.

In the radiotherapy apparatus according to the present invention, even during radiation irradiation radiotherapy, it is possible to monitor the state of the radiotherapy field in real time by the real-time imager (X-ray system) which operates in linkage to the X-ray head (radiation irradiating head).

Also, in the radiotherapy apparatus according to the present invention, the sensor array (image detector) of the real-time imager (X-ray system) is located on the X-ray head (radiation irradiating head) side and operates in linkage with the movement of the X-ray head. Consequently, it is possible to eliminate the influence of the therapeutic radiation to the sensor array.

Also, a set of X-ray source and sensor arrays has a fixed positional relationship to the X-ray head 10. Therefore, it is possible to greatly reduce the burdens of acquiring the diagnostic images or the burdens of the operation of the real-time imager.

In addition, because the sensor array is mounted to the X-ray head side, the therapeutic X-ray 3a, which is an extremely strong X-ray, is not incident on the sensor array.

Furthermore, in the radiotherapy apparatus of the present invention, the O-type gantry is used. Consequently, the X-ray head (radiation irradiating head) can move in the extremely wide range of the ⅝ spherical shell, and is able to irradiate the radiation to the radiotherapy field from any desired angle. In addition, the O-type gantry has a stable structure and high strength. Consequently, it has few problems of apparatus deformation or inertia, and positioning of the X-ray head and sights alignment of radiation irradiation can be accurately carried out.

Furthermore, when the radiotherapy field in the radiotherapy moves, quick sight alignment is carried out from a wide range by the gimbal ring mechanism, and it is possible to irradiate radiation to the radiotherapy field while tracking the radiotherapy field quickly.

Also, because the radiotherapy apparatus of the present invention can accurately irradiate radiation, it is possible to reduce the radiation dose while increasing the therapeutic effects. That is, it is possible to alleviate burdens to the patient.

Second Embodiment

Figure 18:
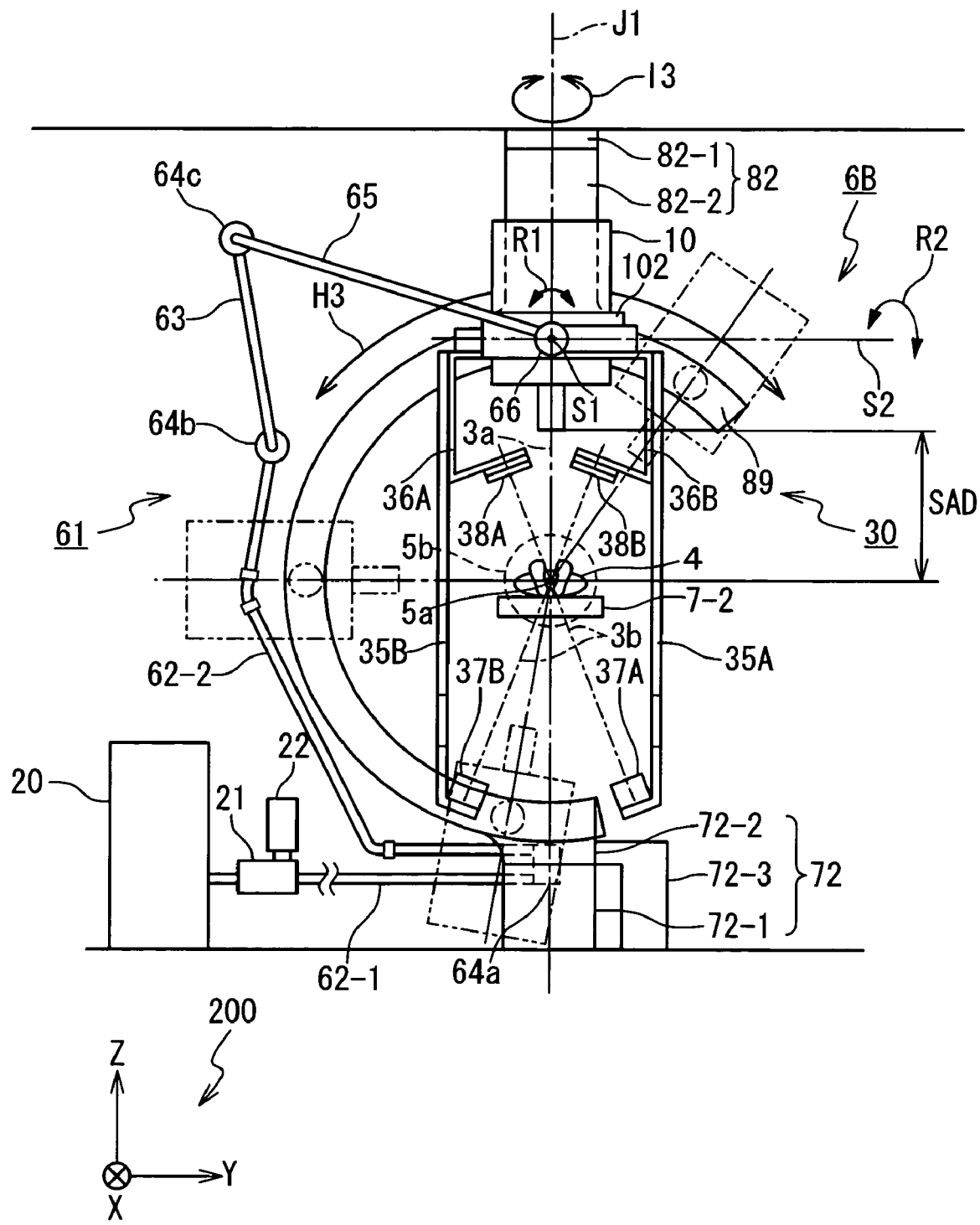
FIG. 18 is a front view showing the configuration of the radiotherapy apparatus according to a second embodiment of the present invention.
Figure 19:
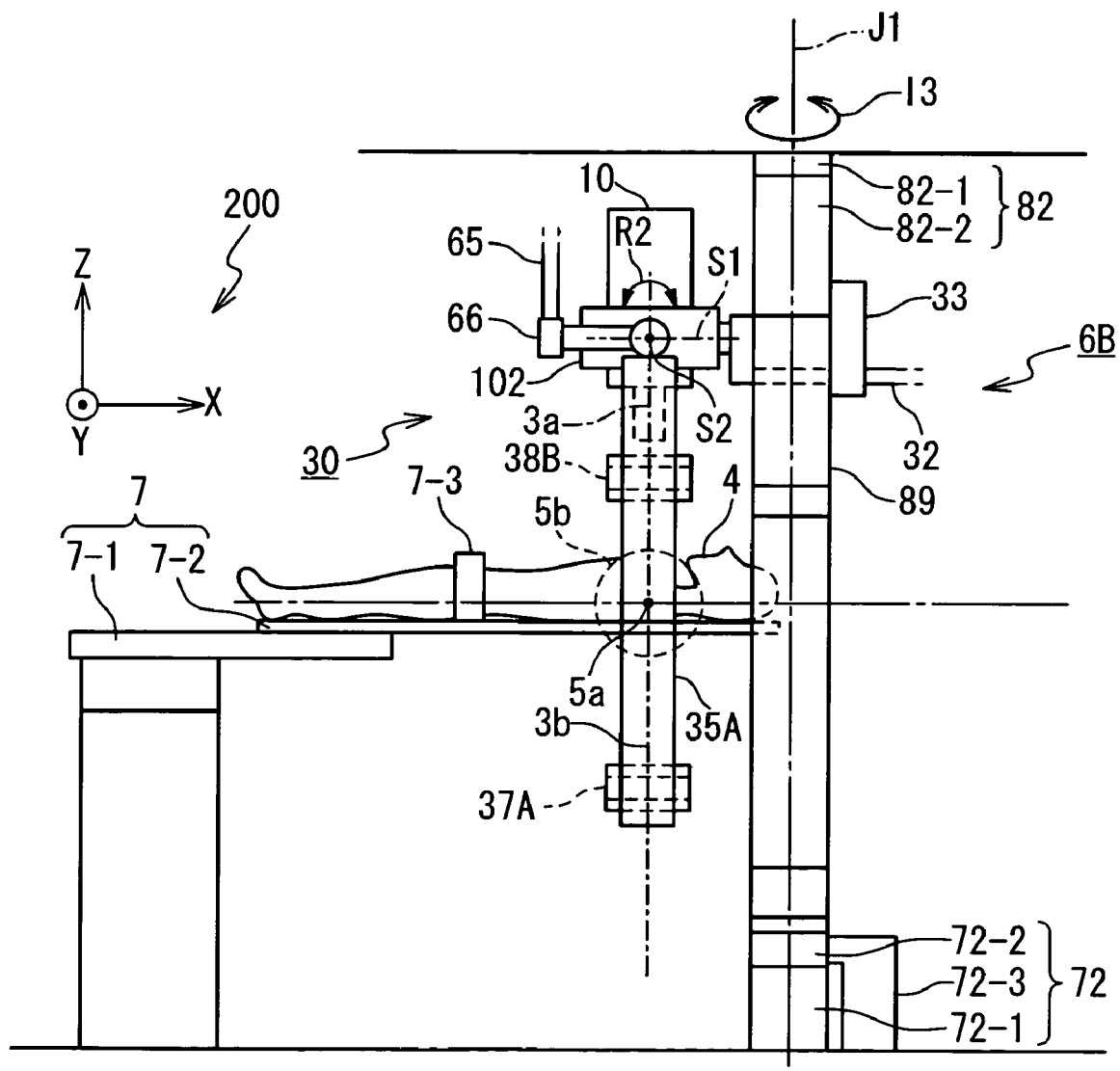
FIG. 19 is a side view showing the configuration of the radiotherapy apparatus according to the second embodiment of the present invention.

The radiotherapy apparatus according to the second embodiment of the present invention will be described in detail below with reference to the attached drawings. FIG. 18 and FIG. 19 are a front view and a side view showing the configuration of the radiotherapy apparatus according to the second embodiment of the present invention. For these diagrams, parts are partly omitted and indicated. Coordinate 200 shows the 3-dimensional orthogonal coordinates which have X-axis, Y-axis, and Z-axis in FIG. 18 and FIG. 19.

A radiotherapy apparatus 6B includes the therapeutic bed system 7, the X-ray head 10, the support frame 67-1, the support frame 67-2, a C-type gantry 89, the waveguide tube system 61, the microwave generating unit 20, and the real-time imager 30.

The C-type gantry 89 includes a head circumferential moving mechanism 33, the gantry rotating mechanism 72, and the upper support mechanism 82.

The C-type gantry 89 (main body) is installed as if it surrounds the periphery of the therapeutic bed 7-2, and has a C-shape. A part is removed from a circle of a pipe with a rectangular cross section. The circle with the part excluded is referred to as a "virtual circle", hereinafter. The C-type gantry 89 is installed on the gantry rotating mechanism 72 to be upright with respect to the horizontal surface (XY plane). The therapeutic bed 7-2 and the X-ray head 10 are disposed in such a manner that the center of the circle comes to the isocenter 5a. The gantry rotating mechanism 72 and the upper support mechanism 82 are same as the first embodiment except that they are intended for the C-type gantry 89.

The head circumferential moving mechanism 33 allows the x-ray head 10 to move in a circumferential direction along the C-type gantry 89 (main body). For the head circumferential moving mechanism 33, a rack and pinion system, and a belt system may be adopted.

Wirings 32 are for control and power supply used for the X-ray head 10, the real-time imager 30, and the head circumferential moving mechanism 33.

The C-type gantry 89 can rotate 340 degrees around the first rotating axis J1. Also, the x-ray head 10 and others (to be described later) can rotate 240 degrees along the C-type gantry 89 with the isocenter 51 set as a center by the head circumferential moving mechanism 33. That is, the X-ray head 10, and others (to be described later) can move in such a manner as to draw about ⅔ sphere (⅔ spherical shell). The C-type gantry 89, the head circumferential moving mechanism 33, and the gantry rotating mechanism 72, and the upper support mechanism 82 are produced of material with large rigidity, for example, stainless steel. The C-type gantry 89 (main body) is 200–400 mm wide, 100–200 mm thick, and 800–1000 mm in radius from the isocenter 5a.

The X-ray head 10 is a radiation irradiating head which irradiates the therapeutic X-rays 3a to the radiation field 5' (diseased part 5). The X-ray head 10 is provided with a small-size electron lineac which radiates the therapeutic X-rays 3a. The X-ray head 10 is movably mounted to the C-type gantry 89 via the head circumferential moving mechanism 33. The X-ray head is provided with a support frame 102 (including the first swing mechanism 131 (to be described later) and the second swing mechanism 132 (to be described later)).

The real-time imager 30 irradiates the diagnostic X-ray 3b to the therapeutic field of the patient 4 and the diagnostic X-ray 3b is a weak fan beam X-ray from the two directions (X-ray sources 37A, 37B). The transmitted images are detected (sensor arrays 38A, 38B). The detected data is image-processed by the image processing unit 31 and 3-dimensional tomography images of the therapeutic field 5 are displayed on the display unit. The real-time imager 30 is controlled by the system control unit 80. The real-time imager 30 includes 2 sets of X-ray sources 37A and 37B and sensor arrays 38A and 38B, as the usual x-ray cameras, and holding frames 35A and 35B as well as holding frames 36A, 36B.

The holding frame 35A and the holding frame 36A are fixedly held to the support frame 102 (or the peripheral member) for the X-ray head 10 on one end, and hold the X-ray source 37A and the sensor array 38A on the other ends. Similarly, the holding frame 35B and holding frame 36B are fixedly held to the support frame 102 (or the peripheral member) or the X-ray head 10 on one end, and hold the X-ray source 37B and the sensor array 38B on the other end. They can move the sets of X-ray sources 37A and 37B and sensor arrays 38A and 38B in conjunction with the movement of the X-ray head. The holding frames 35A and 35B and the holding frames 36A and 36B are made of material with large rigidity such as stainless steel.

The sensor array 38A is located in the vicinity of the X-ray head 10 on one end with the plane perpendicular to the virtual circle including the J1 axis as a boundary. By this, the sensor array 38A does not receive strong X-rays from the X-ray head 10. The perpendicular line from the center portion of the sensor plane is directed to the isocenter 5a, and the X-ay source 37A is disposed on the extension. Similarly, the sensor array 38B is mounted on one end of the holding frame 36B with the plane perpendicular to the virtual circle including the J1 axis therebetween. The sensor array 38B is located in the vicinity of the X-ray head 10 on the other end with the plane perpendicular to the virtual circle including the J1 axis as a boundary. By this, the sensor array 38B does not receive strong X-rays from the X-ray head 10. The perpendicular line from the center portion of the sensor plane is directed to the isocenter 5a, and the X-ray source 37B is disposed on the extension.

The sensor arrays 38A and 38B receive the diagnostic X-ray 3b which penetrates the patient 4. The sensor arrays 38A and 38B are fixed and disposed on the circumference of a circle with the isocenter 5a as the center, which surrounds the diagnostic space to which the patient 4 is disposed. The sensor arrays 38A and 38B are provided with a large number of high-sensitivity CdTe sensors, and provide 0.5 mm resolution. Also, the irradiation time of diagnostic X-ray 3b is 0.01 seconds per shot.

The distance between each of the X-ray sources 37A and 37B and the sensor arrays 38A and 38B and the isocenter 5a is smaller than the distance between the X-ray head 10 and the isocenter 5a. That is, since the X-ray source and the sensor array are located close to the diseased part 5, the picture quality of the diagnostic image is improved. Also, it is possible to take a wide movable range of the X-ray head 10 on the C-type gantry 89.

It is preferable that the angle between the perpendicular line that passes the isocenter 5a from the center part of the sensor array 38A surface and the perpendicular line that passes the isocenter 5a from the center part of the sensor array 38B surface is between 20 degrees and 90 degrees, and more preferably between 40 degrees and 60 degrees. This is set on the basis of the conditions in which the X-ray head 10, the X-ray source 37A and the X-ray source 37B properly operate without affecting each other and diagnostic images with sufficient accuracy are obtained.

The X-ray source 37A and the X-ray source 37B are located on opposite sides with respect to the plane perpendicular to the virtual circle including the J1 axis. The sensor array 38A and the sensor array 38B are same. By this, it is possible to quickly and accurately grasp the movement of each portion in the body of the patient 4.

Also, the real-time imager 30 and the C-type gantry 89 are mechanically tightly connected and have a common coordinate reference.

Because other functions and components are the same as those of the real-time imager 74 of the embodiment 1 and the description will be omitted.

Through the above-mentioned 3-axis drives (I3, H3), the X-ray head 10 can make isocentric motions (X-ray head 10 is directed to the isocenter 5a) on the ⅔ spherical shell with the isocenter 5a as a center. Furthermore, through the 2-axis drives (R1, R2), the X-ray head 10 can make pseudo-nonisocentric motions on the ⅔ spherical shell (X-ray head 10 is directed to a desired point in the three dimensional region 5b (see FIG. 18) in the surrounding vicinity of the isocenter 5a). Because this pseudo-nonisocentric motion is a swing movement around the inertia center of the X-ray head 10, the motion is markedly quick, as compared to the isocentric motion. Through the pseudo-nonisocentric high-responsive quick tracking motion, it is possible to allow the head sight to track at a high response and precisely even for the quick motion such as heart pulses.

Because the therapeutic bed system 7, the support frame 102, the microwave generating unit 20 and the waveguide tube system 61 are same as those of the first embodiment, the description of the details will be omitted.

Also, the X-ray head 10 in FIGS. 3A to 3C and FIG. 4 and the 2-axis swing mechanism of the X-ray head 10 in FIG. 5 and FIGS. 6A to 6E, and the rotary RF coupler in FIGS. 7 to 9 are exactly described in the first embodiment, and the description of them will be omitted.

Now, the control system of the radiotherapy apparatus according to the second embodiment of the present invention will be described. FIG. 10 is a block diagram showing the control system of the radiotherapy apparatus according to the embodiment of the present invention.

The control system according to this embodiment includes the therapeutic bed system 7, the X-ray head system 8, the real-time imager 30, the image processing unit 31, the microwave generating unit 20, the system control unit 80, and the system utility 90. Practically, the system control unit 80 controls the whole of the apparatus. However, the therapy apparatus in the second embodiment is almost same as that of the first embodiment, and the different points are in that the real-time imager is the real-time imager 30, and the C-type gantry 89, the head circumferential moving mechanism 33, and the gantry rotating mechanism 72 are included in the isocentric drive mechanism of the X-ray head system 8. Therefore, the description of the details will be omitted.

Referring now to the attached drawings, the operation of the radiotherapy apparatus according to the second embodiment of the present invention will be described. The operation of the radiotherapy apparatus in the second embodiment is almost the same as that of the first embodiment and the different points are in that the real-time imager is the real-time imager 30 and the C-type gantry 89 and the head circumferential moving mechanism 33 are used. Therefore, the description will be omitted.

According to the radiotherapy apparatus according to the present invention, effects similar to those of the first embodiment can be obtained.

Third Embodiment

Figure 20:
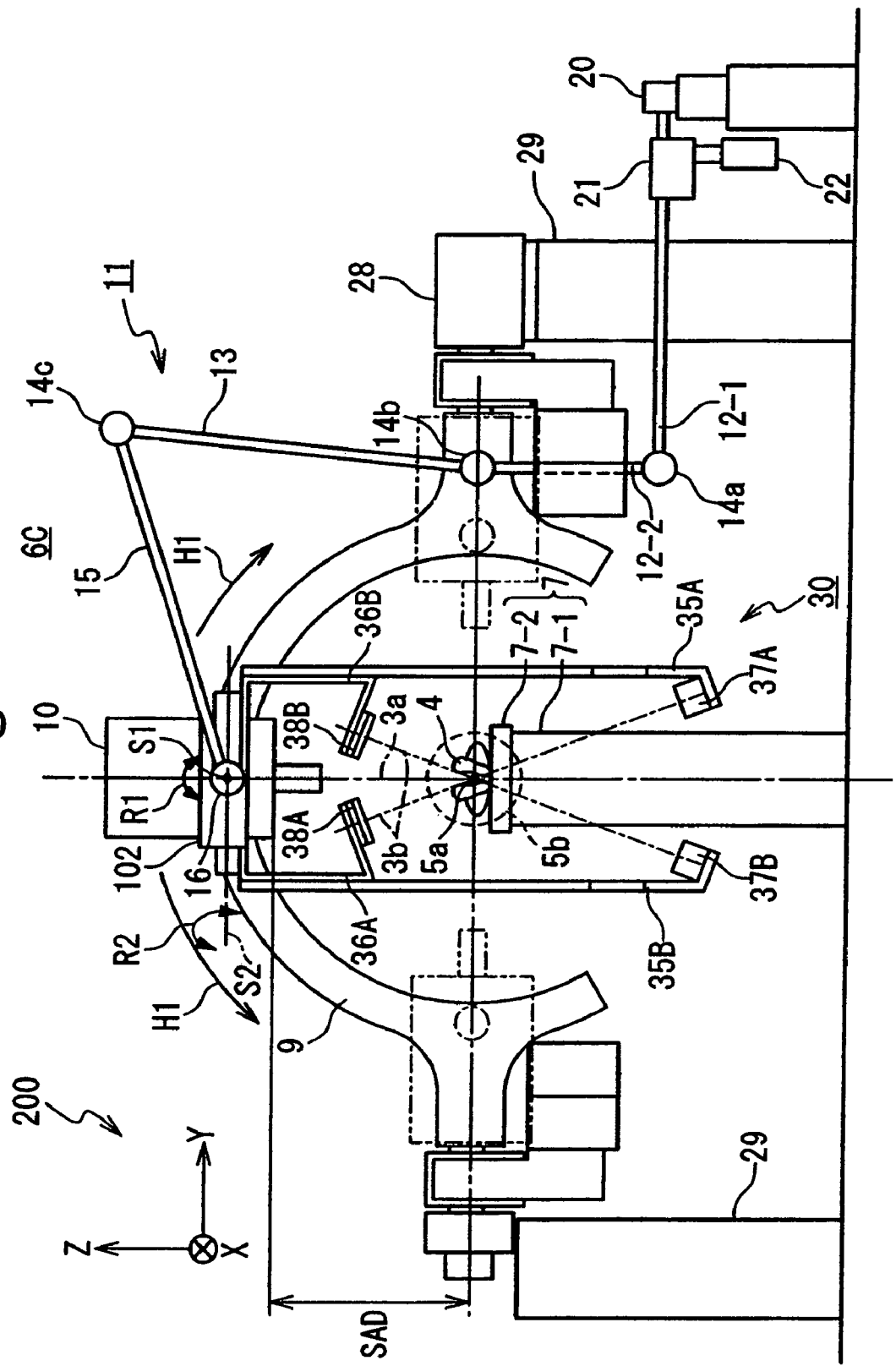
FIG. 20 is a front view showing the configuration of the radiotherapy apparatus according to a third embodiment of the present invention.
Figure 21:
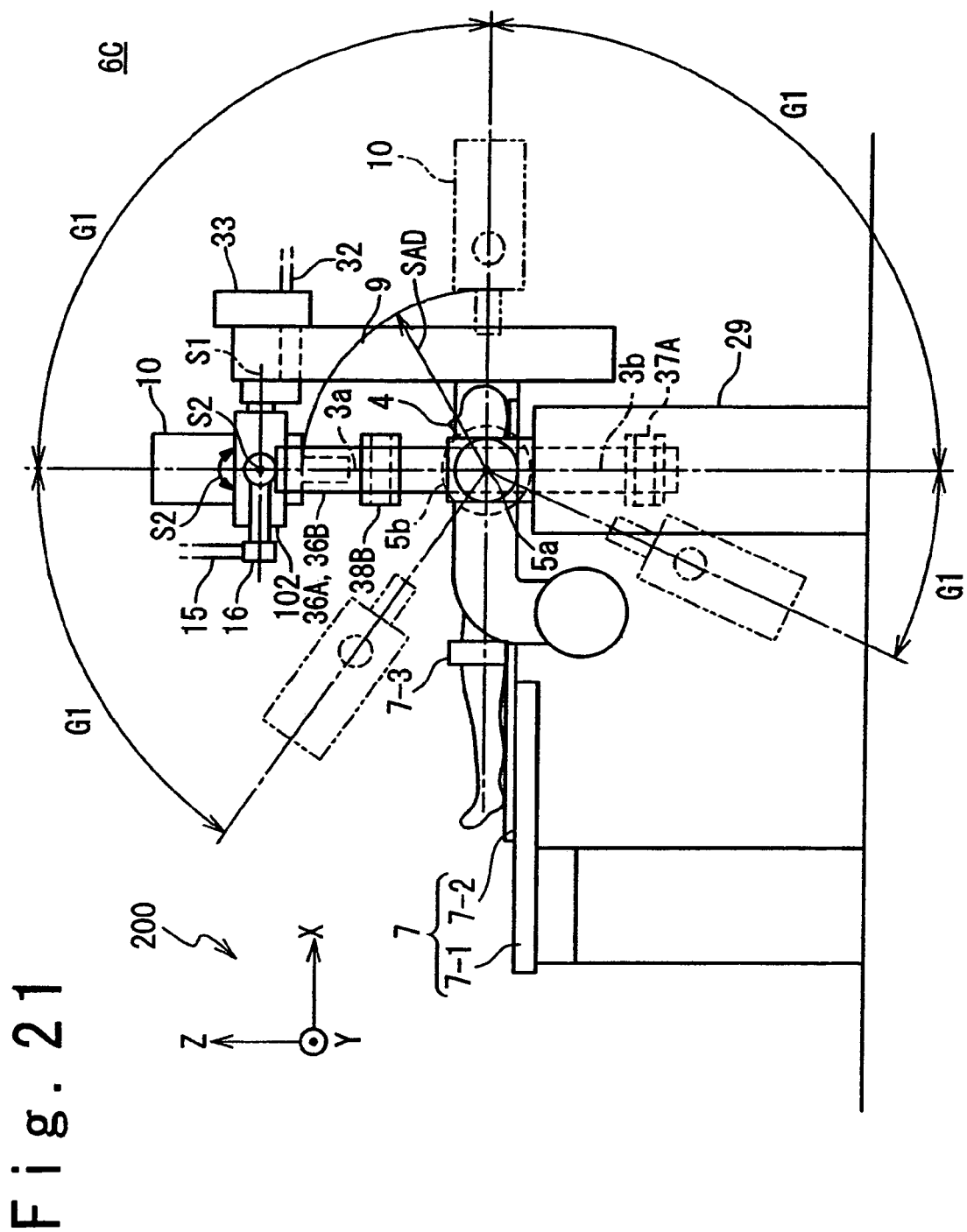
FIG. 21 is a side view showing the configuration of the radiotherapy apparatus according to the third embodiment of the present invention.

Referring now to the attached drawings, a radiotherapy apparatus according to the third embodiment of the present invention will be described in detail. FIG. 20 and FIG. 21 are a front view and a side view showing the configuration of the radiotherapy apparatus according to the third embodiment of the present invention. For the drawings, parts are partly omitted and indicated. The coordinate 200 shows the three-dimensional orthogonal coordinates in the X-axis, Y-axis, and Z-axis directions in FIG. 20 and FIG. 21.

A radiotherapy apparatus 6C includes the therapeutic bed system 7, the X-ray head 10, the support frame 102, an Ω-type gantry 9, the waveguide tube system 61, the microwave generating unit 20, the support bed 29, and the real-time imager 30.

The Ω-type gantry 9 includes a gantry tilting mechanism 28, the head circumferential moving mechanism 33, and the wiring 32. The Ω-type gantry 9 is provided with a semicircular ring which forms an upper half arc on the upper side from the therapeutic bed 7-2 and is installed as if it strides over the therapeutic bed 7-2. A gantry tilting axis 26 is an axis in the Y-axis direction that connects both ends of the semicircle to the center, and the circle center coincides with the isocenter 5a.

A gantry tilting mechanism 28 tiltably supports the Ω-type gantry 9. The gantry tilting mechanism 28 can tilt the Ω-type gantry 9 as shown by G1 in FIG. 21 around the gantry tilting axis 26, in a range from +60 degrees (position tilted in the X-axis negative direction) to −210 degrees (position tilted in the Z-axis negative direction and then tilted further to the X-axis positive direction), by setting the upright position in the Z-axis positive direction to 0 degrees. That is, the Ω-type gantry 9 moves as if it draws a ¾ sphere (¾ spherical shell) with the isocenter 5a set as a center. The Ω-type gantry 9 is made of material with large rigidity, for example, stainless steel, and is 200–400 mm wide, 20–30 mm thick, and 800–1000 mm in radius from the isocenter 5a.

The head circumferential moving mechanism 33 allows the x-ray head 10 to move in the circumferential direction on the semi-arc of the Ω-type gantry 9 along the Ω-type gantry 9. A rack and pinion system and belt system may be adopted for the head circumferential moving mechanism 33.

The wirings 32 are wirings for control and power supply used for the X-ray head 10, real-time imager 30, and the head circumferential moving mechanism 33.

Through the above-mentioned 3-axis drives (G1, H1), the X-ray head 10 can perform an isocentric motion (the X-ray head 10 is directed to the isocenter 5a) on the ¾ spherical shell with the isocenter 5a as a center. Furthermore, through the above-mentioned 2-axis drives (R1, R2), the X-ray head 10 can perform a pseudo-nonisocentric motion on the ¾ spherical shell (the X-ray head 10 is directed to a desired point in the three dimensional region 5b (see FIG. 20) in the surrounding vicinity of the isocenter 5a). Because this pseudo-nonisocentric motion is a swing operation around the inertia center of the X-ray head 10, the motion is markedly quick, as compared to the isocentric motion. Through the pseudo-nonisocentric high-responsive quick tracking motion, it is possible to allow the head sight to track at a high response and precisely even for quick motion such as heart pulses.

The waveguide tube system 11 is a waveguide to supply microwave generated by the microwave generating unit 20 to the X-ray head 10. The waveguide tube system forms a link mechanism by connecting a link arm 12-1, an articulation 14a, a link arm 12-2, an articulation 14b, a link arm 13, an articulation 14c, a link arm 15, an articulation 16, and the X-ray head 10 to one another. The articulation 14a, the articulation 14b, the articulation 14c, and the articulation 16 can rotate around the axis in the X-axis direction. It should be noted that the X-ray head 10 at the link tip section slides along the Ω-type gantry 9 by the head circumferential moving mechanism 33, and is swung around the articulation 16 by the first swing mechanism 131.

The articulations 14a, 14b, 14c, and 16 include a rotary RF coupler 50 (to be described later) which transmits microwaves through axial rotation. The link arms 12-1, 12-2, 13, and 15 include the waveguide 51 (to be described later) and electromagnetically communicate by the articulations 14a through 14c, and 16. The microwave generated in the microwave generating unit 20 is supplied to the X-ray head 10 via the articulation 14a—the link arm 12—the articulation 14b—the link arm 13—the articulation 1c—the link arm 15—the articulation 16.

Because the therapeutic bed system 7, the support frame 102, and the microwave generating unit 20 are same as those of the first embodiment, the explanation will be omitted. Also, the X-ray head 10 and the real-time imager 30 are same as in the second embodiment. Further, the X-ray head 10 in FIGS. 3A to 3C and FIG. 4 and the 2-axis swing mechanism of the X-ray head 10 in FIGS. 5 and 6A to 6E, and the rotary RF coupler in FIG. 7 to FIG. 9 are exactly described in the first embodiment, and their details will be omitted.

Now, the control system of the radiotherapy apparatus according to the third embodiment of the present invention will be described. FIG. 10 is a block diagram showing the control system of the radiotherapy apparatus according to the third embodiment of the present invention.

The control system according to this embodiment includes the therapeutic bed system 7, the X-ray head system 8, the real-time imager 30, the image processing unit 31, the microwave generating unit 20, the system control unit 80, and the system utility 90. Practically, a system configuration in which the system control unit 80 administers and controls the whole is adopted. Here, except that the Ω-type gantry 9, the head circumferential moving mechanism 33, and the gantry tilting mechanism 28 are included in the isocentric drive mechanism of the X-ray head system 8, all components are same as that of the second embodiment, and the details will be omitted.

Referring now to the attached drawings, the operation of the embodiment of the radiotherapy apparatus according to the present invention will be described. With respect to the operation of the radiotherapy apparatus in the third embodiment, except that the Ω-type gantry 9 and the gantry tilting mechanism 28 are used, all others are same as that of the second embodiment (including the description of FIG. 11A to FIG. 17), and the details will be omitted.

According to the radiotherapy apparatus according to the present invention, the effects similar to those of the second embodiment can be obtained.

Fourth Embodiment

Figure 22:
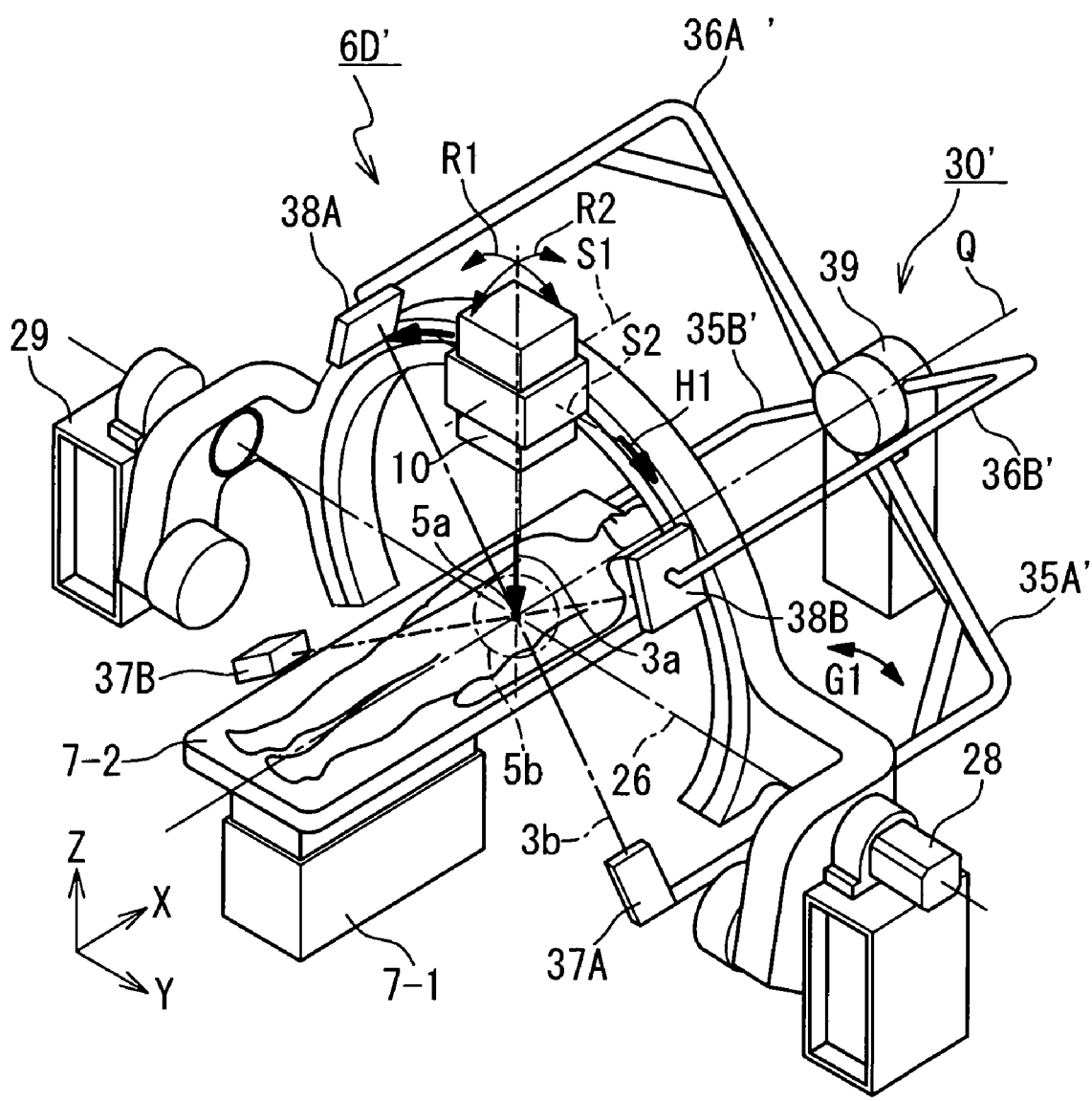
FIG. 22 is a perspective view showing the configuration of the radiotherapy apparatus according to a fourth embodiment of the present invention.

Referring now to the attached drawings, a fourth embodiment of the radiotherapy apparatus according to the present invention will be described in detail. FIG. 22 is a perspective view showing the configuration of the radiotherapy apparatus according to the fourth embodiment of the present invention. For the drawings, parts are partly omitted and indicated. Coordinate 200 shows the three-dimensional orthogonal coordinates in the X-axis, Y-axis, and Z-axis directions in FIG. 22.

A radiotherapy apparatus 6D includes the therapeutic bed system 7, X-ray head 10, the support frame 102, the Ω-type gantry 9, the waveguide tube system 11 (not shown), the microwave generating unit 20 (not shown), the support bed 29, and a real-time imager 30'.

The configuration of the present embodiment is same as the third embodiment except for the real-time imager 30'. This real-time imager 30' includes a rotation drive mechanism 39, holding frames 35A', 35B', holding frames 36A', 36B', and a set of 2 sets of X-ray sources 37A' and 37B' and the sensor arrays 38A' and 38B', which are usual x-ray cameras.

The holding frames 35A' and 35B' have their one ends connected to X-ray sources 37A' and 37B' and the other ends to the rotation drive mechanism 39. Similarly, the holding frames 36A', 36B' have one ends connected to sensor arrays 38A', 38B' and the other ends to the rotation drive mechanism 39.

The sensor array 38A' is located in the vicinity of one side of the X-ray head 10 in the Y-axis direction. The perpendicular line from the center portion of the sensor plane is directed to the isocenter 5a, and the X-ray source 37A' is disposed on the extension. Similarly, the sensor array 38B' is mounted in the vicinity of the other side in the Y-axis direction of the X-ray head 10. The perpendicular line from the center portion of the sensor plane is directed to the isocenter 5a, and the X-ray source 37B' is disposed on the extension.

The rotation drive mechanism 39 rotates the holding frames 35A' and 35B', and the holding frames 36A' and 36B' around the real-time imager rotating axis Q which passes the isocenter 5a and parallel to the X-axis, such that the two sets of X-ray sources 37A' and 37B' and the sensor array 38A' and 38B' come to the desired position. In this case, the rotation drive mechanism rotates the holding frames 35A' and 35B' and the holding frames 36A' and 36B' in conjunction with the movement of the X-ray head 10 so that the two sets of X-ray sources 37A' and 37B' and sensor arrays 38A' and 39B' do not interfere with the movement of the X-ray head 10.

The two sets of X-ray sources 37A' and 37B' and 38A' and 38B' are controlled to hold a predetermined angle. An angle made by the sensor array 38A' or 38B'—the isocenter 5a—X-ray head 10 as a predetermined angle is between 60 degrees and 20 degrees and preferably, between 45 degrees and 30 degrees. This is set on the basis of the conditions in which the X-ray head 10, the X-ray source 37A' and the X-ray source 37B' properly operate without affecting one another and diagnostic images with sufficient accuracy are obtained. It should be noted that the two sets of X-ray sources 37A' and 37B' and the sensor arrays 38A' and 38B' may be controlled independently, respectively, if their visual lines of the sets of X-ray source and sensor array do not coincide.

Because other configurations and operations of the real-time imager 30' are same as the real-time imager 30, the details will be omitted. Also, because the configuration and operation of the present embodiment is same as that of the third embodiment except for the real-time imager 30', the details will be omitted. According to the radiotherapy apparatus of the present invention, it is possible to obtain the same effects as those of the third embodiment.

Also, since the set of X-ray sources and sensor arrays are mounted to a mechanism different from the X-ray head, the burden on the gantry and X-ray head are small.

Fifth Embodiment

Figure 23:
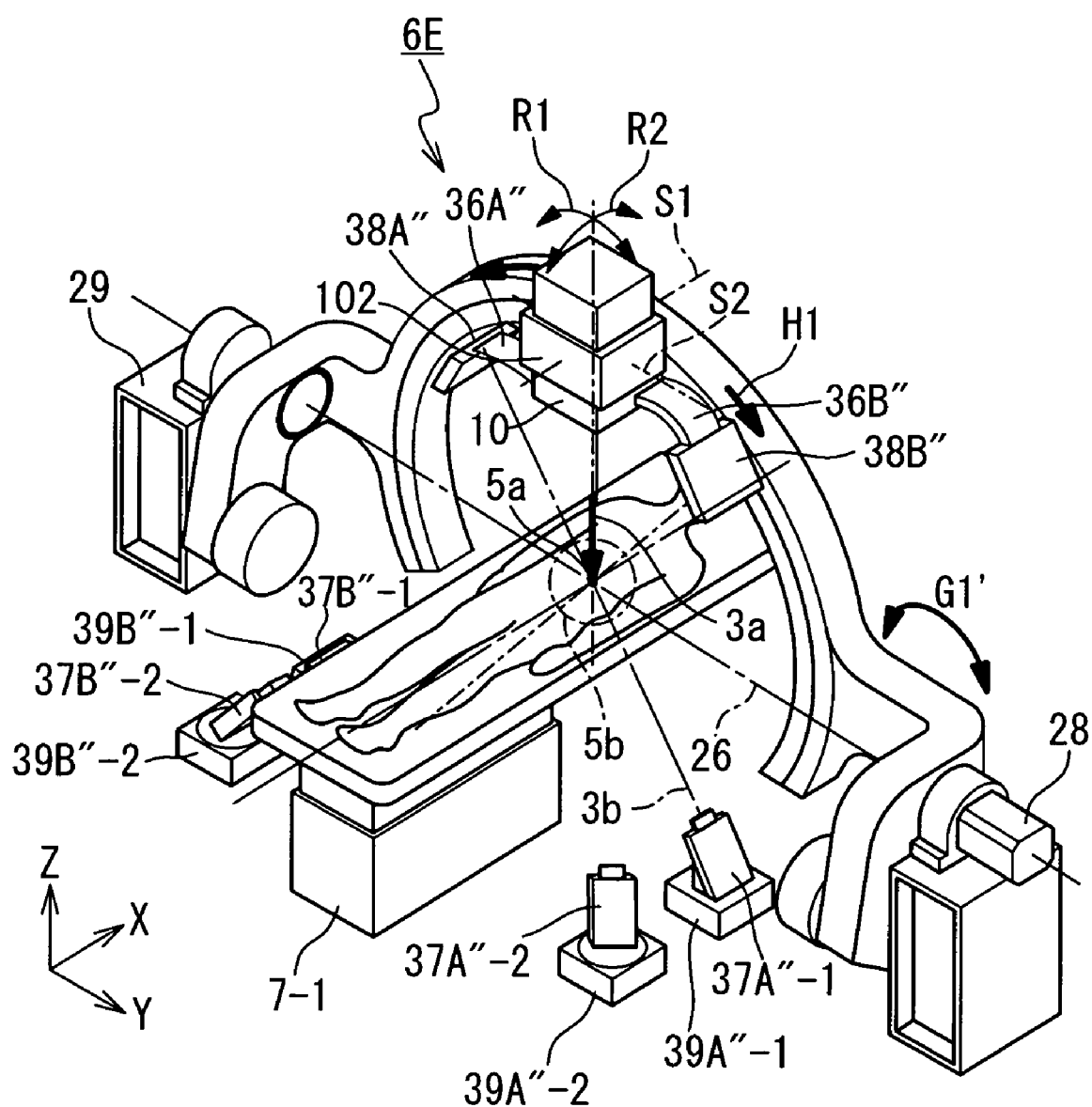
FIG. 23 is a perspective view showing the configuration of the radiotherapy apparatus according to a fifth embodiment of the present invention.

Referring now to the attached drawings, a fifth embodiment of the radiotherapy apparatus according to the present invention will be described in detail. FIG. 23 is a perspective view showing the configuration of the radiotherapy apparatus according to the fifth embodiment of the present invention. For the drawing, parts are partly omitted and indicated. The coordinate 200 shows the three-dimensional orthogonal coordinates which have X-axis, Y-axis, and Z-axis in FIG. 23.

The radiotherapy apparatus 6E includes the therapeutic bed system 7, the X-ray head 10, the support frame 102, the Ω-type gantry 9, the waveguide tube system 11 (not shown), the microwave generating unit 20 (not shown), the support bed 29, and the real-time imager.

The configuration of the present embodiment is same as the third embodiment except that the real-time imager differs.

The Ω-type gantry 9 includes the gantry tilting mechanism 28, the head circumferential moving mechanism 33, and the wiring 32. The gantry tilting mechanism 28 tiltably supports the Ω-type gantry 9. The gantry tilting mechanism 28 can tilt the Q-type gantry 9 as shown by G1' in FIG. 23 around the gantry tilting axis 26 in a range from 0 degrees to 90 degrees (position tilted in the Z-axis negative direction and then tilted further to the X-axis positive direction), by setting the upright position in the Z-axis positive direction to 0 degrees. That is, the Ω-type gantry 9 moves as if it draws a ¼ sphere (¼ spherical shell) with the isocenter 5a set as a center. The Ω-type gantry 9 is made of material with large rigidity, for example, stainless steel, and is 200–400 mm wide, 20–50 mm thick, and 800–1000 mm in radius from the isocenter 5*a*.

The head circumferential moving mechanism 33 and the wiring 32 are same as those of the fourth embodiment and the description will be omitted.

By the above-mentioned 3-axis drives (G1', H1), the X-ray head 10 can perform isocentric motion (the X-ray head 10 is directed to the isocenter 5*a*) on the ¼ spherical shell with the isocenter 5*a* as a center. Furthermore, by the above-mentioned 2-axis drives (R1, R2), the X-ray head 10 can perform pseudo-nonisocentric motion on the ¾ spherical shell (X-ray head 10 is directed to a desired point in the three dimensional region 5*b* (see FIG. 23) in the surrounding vicinity of the isocenter 5*a*). Because this pseudo-nonisocentric motion is a swing operation around the inertia center of the X-ray head 10, motion is markedly quick, as compared to the isocentric motion. Through the pseudo-nonisocentric high-responsive quick tracking motion, it is possible to allow the head sights to track at a high response and precisely even for the quick motion such as heart pulses.

The real-time imager includes rotation drive mechanisms 39A"-1, 39A"-2, 39B"-1 and 39B"-2, X-ray source 37A"-1 and 37A"-2 and 37B"-1 and 37B"-2 which are mounted to each of the rotation drive mechanisms, respectively, holding frames 36A" and 36B", and sensor arrays 38" and 38B".

The holding frames 36A" and 36B" have their one ends connected to the holding frame 102 of the X-ray head 10 and their other ends to sensor arrays 38A", 38B". That is, the holding frames 36A" and 36B" are fixed to the X-ray head 10 and can move in conjunction with the X-ray head 10. The angle made by the sensor array 38A" or sensor array 38B" and the isocenter 5*a* and X-ray head 10 are between 90 degrees and 20 degrees and more preferably, between 60 degrees and 30 degrees.

The sensor array 38A" is located in the vicinity of one side of the X-ray head 10 in the Y-axis direction. The perpendicular line from the center portion of the sensor plane is directed to the isocenter 5*a*. Similarly, the sensor array 38B" is mounted in the vicinity of the other side in the Y-axis direction of the X-ray head 10. The perpendicular line from the center portion of the sensor plane is directed to the isocenter 5*a*.

The rotation drive mechanisms 39A"-1, 39A"-2, 39B"-1 and 39B"-2 are installed on the floor surface. The posture of each X-ray sources is controlled so that the directions of X-ray sources 37A"-1, 37A"-2, 37B"-1 and 37B"-2 become the directions of the predetermined sensor arrays 38A" or 38B".

Each of X-ray sources 37A"-1, 37A"-2, 37B"-1 and 37B"-2 are mounted on the rotation drive mechanisms 39A"-1, 39A"-2, 39B"-1 and 39B"-2. By the system control unit 80, the optimum two X-ray sources are selected from the plurality of X-ray sources based on the position of the X-ray head 10 (in FIG. 23, four of X-ray sources 37A"-1, 37A"-2, 37B"-1 and 37B"-2). In this case, the optimum two X-ray sources are designed to satisfy the conditions that the diagnostic X-ray 3*b* is irradiated to the peripheral region (vicinity of the isocenter 5*a*) including the diseased part 5 and the transmission X-ray reaches sensor arrays. This selection of the optimum X-ray sources is carried out every time the portal (irradiation direction) of the therapeutic X-ray 3*a* is changed (this is not carried out in the tracking motion). Also, the two sets of selected X-ray sources and sensor arrays are controlled to prevent their visual lines from coinciding.

Because other configurations and operations of the real-time imager are the same as the real-time imager 30, the details will be omitted. Also, because the configuration and operation of the present embodiment is the same as that of the third embodiment except for the real-time imager, the details will be omitted for other configurations.

According to the radiotherapy apparatus of the present invention, it is possible to obtain effects the same as those of the third embodiment. Also, since the set of X-ray sources and sensor arrays are mounted to a mechanism different from the X-ray head, the burdens on the gantry and X-ray head are small.

According to the present invention, pseudo-nonisocentric radiotherapy is made possible by allowing the head section itself to carry out 1-axis or 2-axis swing operation around an appropriate rotation center such as its inertia center in addition to the isocentric motion of the whole radiation head. Also, the same effect can be achieved, compared with completely nonisocentric radiotherapy apparatus. Also, the X-ray head can follow the movement of the radiation field caused by breathing or heart pulses at high speed.

According to the present invention, the nonmagnetic type precision inspection apparatus enables high-accuracy control of conditions of radiation irradiating position, irradiation time, and others while the radiotherapy field is being confirmed. Consequently, the apparatus can not only be applied to the head which has no movement in the organ itself but also accurately irradiate the X-ray to small seats of disease of organs with movements such as heart and lungs, and the application can be increased in the radiotherapy field.

According to the present invention, unlike a cantilever type robot arm which causes many problems from the viewpoint of rigidity, a high-strength high-rigidity radiation head support structure can be adopted, and high absolute accuracy can be mechanically guaranteed. Consequently, the desired efficient therapy is made possible.

It is a problem from the viewpoint of patient safety to apply a general-purpose industrial robot arm which has an excessive degree of freedom that exceeds the degree of freedom required for nonisocentric radiotherapy. That is, in the event of accidents such as an erroneous operation of the robot arm, the robot arm or the radiation irradiating head at its tip section may come in contact with a patient, possibly causing traumatic danger to the patient. On contrary, the radiotherapy apparatus of the present invention has the movable range restricted and can secure absolute safety to the patient.

In the conventional technique, the radiation field cannot be monitored in real time during radiotherapy, and irradiation based on estimation is forced to be carried out. However, according to the present invention, it becomes possible to monitor the radiation field in real time during radiotherapy by an imager such as usual X-ray cameras, X-ray CT, PET, and DSA, and high reliability and high safety radiotherapy is achieved.

In addition, the image tracking operation is carried out on the basis of the radiation field images obtained in real time and follow-up irradiation to moving radiation fields is made possible.

By the man-machine interface with a doctor or physician shown in embodiments of the present invention, radiotherapy with superb safety and reliability is achieved.

In the radiotherapy apparatus of the present invention, it becomes possible to monitor the radiation field condition in real time without interfering with the X-ray head (radiation irradiating head) by the real-time imager (X-ray system) which operates in linkage with the X-ray head (radiation irradiating head) even while radiotherapy is being carried out by irradiating the seat of disease with radiation.

What is claimed is:

1. A radiotherapy apparatus comprising:
   a gantry section;
   an irradiation head section configured to irradiate therapeutic radiation to a therapeutic field of a target subject;
   an X-ray source section movably provided on said gantry section and configured to irradiate diagnostic X-rays to the therapeutic field of the target subject; and
   a sensor array section movably provided on said gantry section and configured to detect the diagnostic X-rays which have transmitted through the target subject and to output diagnostic X-ray image data based on the detected diagnostic X-rays;
   an image processing unit configured to generate diagnostic images of the therapeutic field based on the diagnostic X-ray image data;
   a head swing mechanism movably provided on said gantry section and configured to swing said irradiation head section such that the therapeutic radiation outputted from said irradiation head section follows the movement of the therapeutic field; and
   a control unit configured to carry out position control of said head swing mechanism based on the diagnostic images, a position of said irradiation head section, and a swing state of said irradiation head section such that the irradiated field of said irradiation head section tracks the therapeutic field, and to control said irradiation head section to irradiate the therapeutic radiation after the position control of said head swing mechanism has been carried out;
   wherein said irradiation head section is movably coupled to said head swing mechanism and said irradiation head section and said head swing mechanism are provided along a line from said gantry section to the therapeutic field;
   wherein said gantry section comprises first and second gantries, and said head swing mechanism is movably provided on an L type gantry and a robot arm as said first gantry and said X-ray source section and sensor array section are provided on said second gantry.

2. The radiotherapy apparatus according to claim 1, wherein said X-ray source section is arranged to be movable in conjunction with movement of said sensor array section.

3. The radiotherapy apparatus according to claim 1, wherein said sensor array section is provided in a vicinity of said irradiation head section.

4. The radiotherapy apparatus according to claim 3, wherein said sensor array section comprises sensor arrays provided on both sides of said irradiation head section.

5. The radiotherapy apparatus according to claim 1, wherein a distance from (a) each of said X-ray source section and said sensor array section to (b) an isocenter is smaller than a distance from (c) said irradiation head to (b) said isocenter.

6. The radiotherapy apparatus according to claim 1, wherein said X-ray source section and said sensor array section are provided at positions symmetrical to each other with respect to said isocenter.

7. A radiotherapy apparatus comprising:
   an irradiation head section movably provided on a gantry and configured to irradiate therapeutic radiation to a therapeutic field of a target subject;
   an X-ray source section configured to irradiate diagnostic X-rays to the therapeutic field of said target subject; and
   a sensor array section, configured to move in conjunction with movement of said irradiation head section, to detect the diagnostic X-rays which have transmitted through the target subject, and to output diagnostic X-ray image data based on the detected diagnostic X-rays;
   a control unit;
   an image processing unit configured to generate diagnostic images of the therapeutic field based on the diagnostic X-ray image data; and
   a head swing mechanism configured to swing said irradiation head section such that the therapeutic radiation outputted from said irradiation head section follows the movement of said therapeutic field,
   wherein:
     said control unit is operable to carry out position control of said head swing mechanism based on said diagnostic images, a position of said irradiation head section, and a swing state of said irradiation head section, such that the irradiated field of said irradiation head section tracks the therapeutic field, and to control said irradiation head section to irradiate the therapeutic radiation after the position control of said head swing mechanism, and
     said control unit is operable to calculate a first coordinate as a coordinate of the therapeutic field in the diagnostic images based on a predetermined image pattern indicating the therapeutic field on the diagnostic images, calculate a second coordinate as a coordinate of the irradiated field based on the position of said irradiation head section and the swing state of said irradiation head section, and carry out the positional control of said head swing mechanism such that the therapeutic field is contained in the irradiated field based on said first and second coordinates.

8. The radiotherapy apparatus according to claim 7, wherein said control unit is operable to carry out the position control of said head swing mechanism and the control of said irradiation head section for each of a plurality of predetermined time periods.

9. The radiotherapy apparatus according to claim 7, wherein said head swing mechanism is operable to swing said irradiation head section around two axes orthogonal to each other.

10. The radiotherapy apparatus according to claim 7, further comprising a head circumferential moving mechanism configured to move said irradiation head section along a ring of said gantry, said gantry being an O-type gantry.

11. The radiotherapy apparatus according to claim 7, further comprising:
    a gantry rotating mechanism configured to rotate said gantry around a vertical axis, said gantry being an O-type gantry.

12. The radiotherapy apparatus according to claim 7, further comprising:
    a microwave generating unit configured to generate microwaves; and
    a waveguide configured to couple said microwave generating unit and said irradiation head section and to guide microwaves from said microwave generating unit to said irradiation head section.

13. The radiotherapy apparatus according to claim 12, wherein said microwave generating unit is configured to generate microwaves belonging to a C band, and said irradiation head section comprises an accelerator tube configured to accelerate electrons of an electron beam with the microwaves.

14. The radiotherapy apparatus according to claim 12, wherein said microwave generating unit is configured to generate microwaves belonging to an X band, and said irradiation head section comprises an accelerator tube configured to accelerate electrons of an electron beam with the microwaves.

* * * * *

EX PARTE REEXAMINATION CERTIFICATE (9823rd)
United States Patent
Hara et al.

(10) Number: US 7,239,684 C1
(45) Certificate Issued: Sep. 3, 2013

(54) RADIOTHERAPY APPARATUS MONITORING THERAPEUTIC FIELD IN REAL-TIME DURING TREATMENT

(75) Inventors: Kenji Hara, Hiroshima (JP); Makoto Akatsu, Hiroshima (JP); Noriyuki Kawata, Hiroshima (JP)

(73) Assignee: Mitsubishi Heavy Industries, Ltd., Minato-Ku, Tokyo (JP)

Reexamination Request:
No. 90/012,592, Sep. 14, 2012

Reexamination Certificate for:
Patent No.: 7,239,684
Issued: Jul. 3, 2007
Appl. No.: 11/067,013
Filed: Feb. 28, 2005

(51) Int. Cl.
*A61N 5/10* (2006.01)
*A61B 5/05* (2006.01)
*A61B 6/00* (2006.01)

(52) U.S. Cl.
USPC .................................. 378/65; 600/427; 606/1

(58) Field of Classification Search
None
See application file for complete search history.

(56) References Cited

To view the complete listing of prior art documents cited during the proceeding for Reexamination Control Number 90/012,592, please refer to the USPTO's public Patent Application Information Retrieval (PAIR) system under the Display References tab.

*Primary Examiner* — Salman Ahmed

(57) ABSTRACT

A radiotherapy apparatus includes an irradiation head section, an X-ray source section and a sensor array section. The irradiation head section irradiates therapeutic radiation to a therapeutic field of a target substance. The X-ray source section irradiates diagnostic X-rays to the therapeutic field of the target subject. The sensor array section detects the diagnostic X-rays which have transmitted the target subject, and outputs diagnostic X-ray image data based on the detected diagnostic X-rays. The sensor array section moves in conjunction with movement of the irradiation head section.

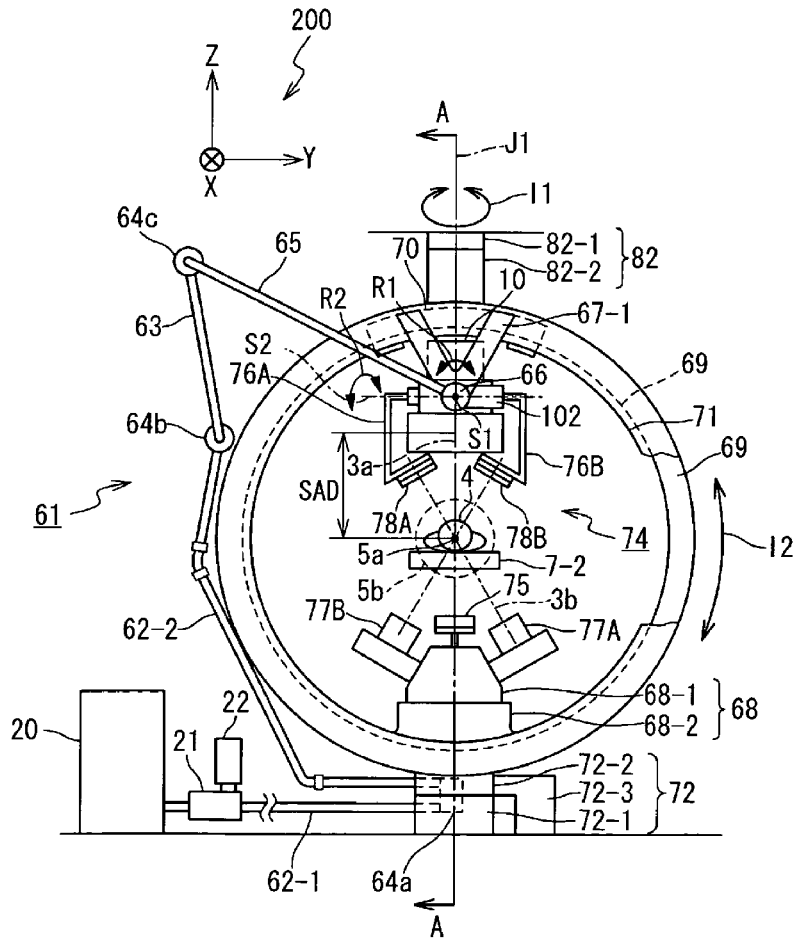

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-6, 10 and 11 are cancelled.

Claim 7 is determined to be patentable as amended.

Claims 8, 9 and 12-14, dependent on an amended claim, are determined to be patentable.

7. A radiotherapy apparatus comprising:
   an irradiation head section movably provided on a gantry and configured to irradiate therapeutic radiation to a therapeutic field of a target subject;
   an X-ray source section configured to irradiate diagnostic X-rays to the therapeutic field of said target subject; and
   a sensor array section, configured to move in conjunction with movement of said irradiation head section, to detect the diagnostic X-rays which have transmitted through the target subject, and to output diagnostic X-ray image data based on the detected diagnostic X-rays;
   a control unit;
   an image processing unit configured to generate diagnostic images of the therapeutic field based on the diagnostic X-ray image data; and
   a head swing mechanism configured to swing said irradiation head section such that the therapeutic radiation outputted from said irradiation head section follows the movement of said therapeutic field,
wherein:
   said control unit is operable to carry out position control of said head swing mechanism based on said diagnostic images, a position of said irradiation head section, and a swing state of said irradiation head section, such that the irradiated field of said irradiation head section tracks the therapeutic field, and to control said irradiation head section to irradiate the therapeutic radiation after the position control of said head swing mechanism, and
   said control unit is operable to calculate a first coordinate as a coordinate of the therapeutic field in the diagnostic images based on a predetermined image pattern indicating the therapeutic field on the diagnostic images, calculate a second coordinate as a coordinate of the irradiated field based on the position of said irradiation head section and the swing state of said irradiation head section, and carry out the positional control of said head swing mechanism such that the therapeutic field is contained in the irradiated field based on said first and second coordinates*;*
*wherein said gantry is an O-type gantry that is mounted with a gantry rotating mechanism that is configured to rotate said O-type gantry around a vertical axis;*
*wherein said O-type gantry comprises driving rings and a head circumferential moving mechanism that is configured to move said irradiation head section along said driving rings of said O-type gantry;*
*wherein said O-type gantry has said driving rings positioned on opposite sides thereof;*
*wherein support frames are fixed to respective said driving rings and extend radially inwardly therefrom to support said head swing mechanism; and*
*said X-ray source section is fixed to said driving rings at a position thereon that is radially opposite to said support frames.*

\* \* \* \* \*